US010314546B2

(12) United States Patent
Lisogurski et al.

(10) Patent No.: US 10,314,546 B2
(45) Date of Patent: Jun. 11, 2019

(54) CAPACITANCE ENHANCED PHYSIOLOGICAL MEASUREMENTS

(71) Applicant: Covidien LP, Mansfield, MA (US)

(72) Inventors: Daniel Lisogurski, Boulder, CO (US); Christopher J. Meehan, Arvada, CO (US); Eric Morland, Erie, CO (US); Friso Schlottau, Lyons, CO (US)

(73) Assignee: Covidien LP, Mansfield, MA (US)

( * ) Notice: Subject to any disclaimer, the term of this patent is extended or adjusted under 35 U.S.C. 154(b) by 321 days.

(21) Appl. No.: 15/259,621

(22) Filed: Sep. 8, 2016

(65) Prior Publication Data
US 2016/0374620 A1 Dec. 29, 2016

Related U.S. Application Data

(63) Continuation of application No. 14/273,764, filed on May 9, 2014, now Pat. No. 9,462,979.
(Continued)

(51) Int. Cl.
*A61B 5/1455* (2006.01)
*A61B 5/00* (2006.01)
*A61B 5/0205* (2006.01)
*A61B 5/026* (2006.01)
*A61B 5/0295* (2006.01)
*A61B 5/0402* (2006.01)
(Continued)

(52) U.S. Cl.
CPC ............ *A61B 5/721* (2013.01); *A61B 5/0059* (2013.01); *A61B 5/0205* (2013.01); *A61B 5/0261* (2013.01); *A61B 5/0295* (2013.01); *A61B 5/0402* (2013.01); *A61B 5/1455* (2013.01); *A61B 5/14551* (2013.01); *A61B 5/6826* (2013.01); *A61B 5/6838* (2013.01); *A61B 5/746* (2013.01); *A61B 7/00* (2013.01); *A61B 5/021* (2013.01); *A61B 5/02405* (2013.01); *A61B 5/02416* (2013.01); *A61B 5/053* (2013.01); *A61B 5/08* (2013.01); *A61B 5/085* (2013.01); *A61B 5/0816* (2013.01); *A61B 5/0826* (2013.01); *A61B 5/11* (2013.01); *A61B 5/14546* (2013.01); *A61B 5/14552* (2013.01); *A61B 2562/0214* (2013.01)

(58) Field of Classification Search
CPC ... A61B 5/1455; A61B 5/14551; A61B 5/721; A61B 5/0205; A61B 5/0295
See application file for complete search history.

(56) References Cited

U.S. PATENT DOCUMENTS

| | | | | |
|---|---|---|---|---|
| 5,368,026 A | * | 11/1994 | Swedlow | A61B 5/14551 600/323 |
| 8,238,994 B2 | * | 8/2012 | Baker, Jr. | A61B 5/14551 600/323 |
| 2014/0058217 A1 | * | 2/2014 | Giovangrandi | A61B 5/14552 600/322 |

* cited by examiner

*Primary Examiner* — Eric F Winakur

(57) ABSTRACT

Systems, methods, apparatuses, and software for measuring and determining physiological parameters of a patient are presented. In one example, a physiological measurement system includes an optical system configured to emit one or more optical signals into tissue of a patient, and detect the one or more optical signals after propagation through the tissue. The physiological measurement system includes a capacitance system configured to apply one or more electric field signals to a single side of the tissue to determine a capacitance signal based at least on changes in the one or more electric field signals, and a processing system configured to process at least the one or more detected optical signals and the capacitance signal to determine a physiological parameter of the patient.

30 Claims, 21 Drawing Sheets

Related U.S. Application Data

(60) Provisional application No. 61/912,998, filed on Dec. 6, 2013.

(51) Int. Cl.
*A61B 7/00* (2006.01)
*A61B 5/024* (2006.01)
*A61B 5/053* (2006.01)
*A61B 5/08* (2006.01)
*A61B 5/11* (2006.01)
*A61B 5/021* (2006.01)
*A61B 5/085* (2006.01)
*A61B 5/145* (2006.01)

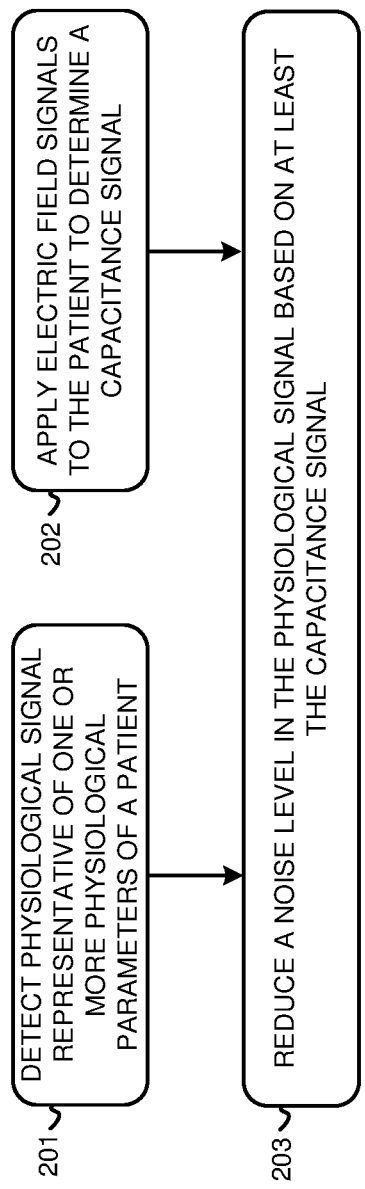

CAPACITANCE ENHANCED PHYSIOLOGICAL MEASUREMENTS

RELATED APPLICATIONS

This patent application is a continuation of U.S. patent application Ser. No. 14/273,764 that was filed on May 9, 2014, and is entitled "CAPACITANCE ENHANCED PHYSIOLOGICAL MEASUREMENTS," which is also related to and claims priority to U.S. Provisional Patent Application No. 61/912,998, titled "CAPACITANCE ENHANCED OPTICAL PHYSIOLOGICAL MEASUREMENTS," filed Dec. 6, 2013, and which is hereby incorporated by reference in its entirety.

TECHNICAL FIELD

Aspects of the disclosure are related to the field of medical devices, and in particular, measuring physiological parameters of tissue.

TECHNICAL BACKGROUND

Various medical devices can non-invasively measure parameters of blood in a patient. Pulse oximetry devices are one such non-invasive measurement device, typically employing solid-state lighting elements, such as light-emitting diodes (LEDs) or solid state lasers, to introduce light into the tissue of a patient. The light is then detected to generate a photoplethysmogram (PPG). These photoplethysmography systems can also measure changes in blood volume of tissue of a patient and calculate various parameters such as heart rate, respiration rate, and oxygen saturation.

However, some conventional optical pulse oximetry devices only measure certain limited blood parameters, and lack the ability to measure other patient physiological parameters. Some optical pulse oximetry devices are also subject to patient-specific noise and inconsistencies which limit the accuracy of such devices. For example, monitoring infants or patients in intensive care units can be difficult. Motion of the patient and other incidental factors can lead to noise and inaccuracies of optical-based measurements. Some optical measurement systems are sensitive to shifts in venous blood volumes, introducing errors into arterial blood measurements.

Capacitive sensing has been employed to measure some physiological parameters by applying electric fields directly through tissue using two-plate capacitors having individual plates positioned on different sides of the tissue. This two-plate capacitive sensing can be combined with optical measurement to determine changes in volume of tissue due to cardiac pulsing.

OVERVIEW

Systems, methods, apparatuses, and software for measuring and determining physiological parameters of a patient are presented. In one example, a physiological measurement system includes an optical system configured to emit one or more optical signals into tissue of a patient, and detect the one or more optical signals after propagation through the tissue. The physiological measurement system includes a capacitance system configured to apply one or more electric field signals to a single side of the tissue to determine a capacitance signal based at least on changes in the one or more electric field signals, and a processing system configured to process at least the one or more detected optical signals and the capacitance signal to determine a physiological parameter of the patient.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

FIG. 2 is a flow diagram illustrating a method of operating a physiological measurement system.

DETAILED DESCRIPTION

Figure 1A:
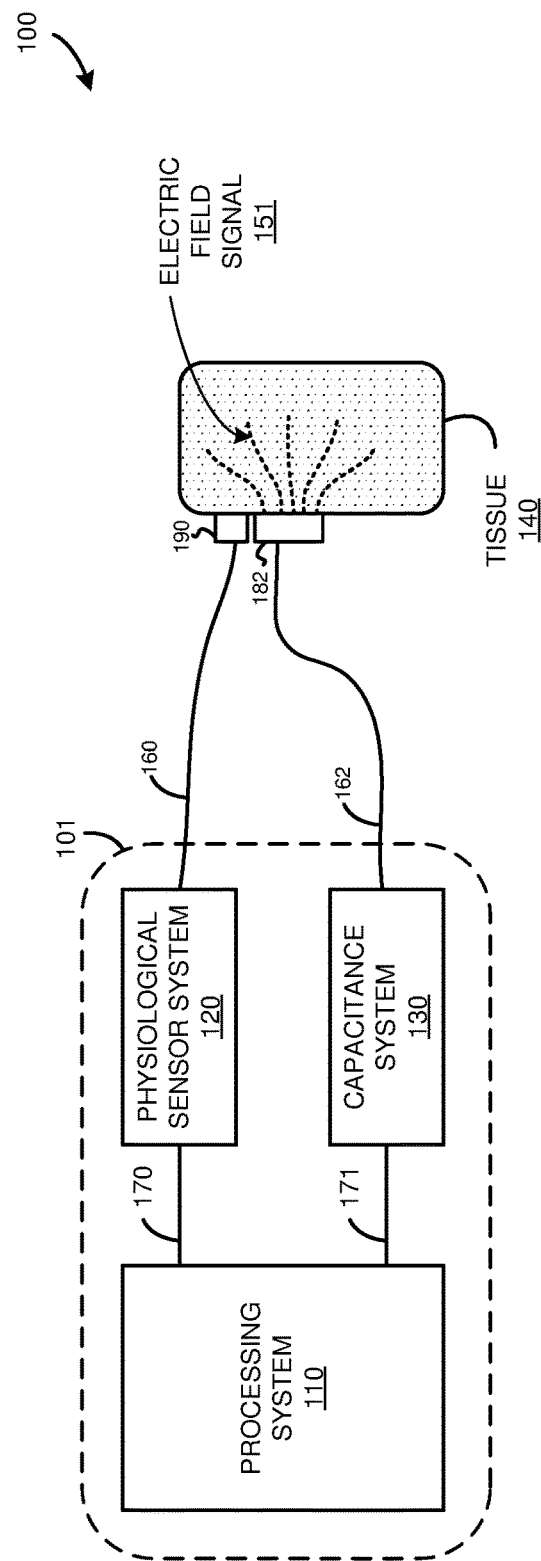
FIG. 1A is a system diagram illustrating a physiological measurement system.

The examples discussed herein include systems, apparatuses, methods, and software for enhanced measurement of physiological parameters in patients. When optical measurements are employed to detect physiological parameters in tissue of a patient, optical signals associated with the optical measurement can be subjected to various interference and noise, such as patient motion artifacts and patient-specific variability. Capacitance-based sensing can be employed to enhance or supplement the optical measurements to provide corrections, data stabilization, or additional sensing capabilities to optical-only measurement systems. In other examples, capacitance measurements are employed to detect physiological parameters in tissue of a patient without relying upon optical measurements.

In addition to the advantages and applications of the capacitance-enhanced optical and capacitance-based systems below, other applications such as fitness band monitors to monitor pulse, breathing rate, heart rate, sweating levels, oxygen levels, or other parameters of subjects performing athletic activities can include these capacitance and optical monitoring systems. For example, such systems are described below with respect to FIGS. 7-9. Other examples include cuff pressure and moisture monitoring systems for tracheal tubes or for monitoring of premature babies.

The physiological parameters measured or determined by the capacitance-enhanced systems can include various plethysmograph (pleth) information, such as photoplethysmograms (PPG), PPG parameters, and temporal variability of PPG parameters (such as pleth morphology and pulse information). The physiological parameters measured or determined by the capacitance-enhanced systems can also include electrocardiography (ECG) information via capacitive sensing, pulse rate, respiratory rate, respiratory effort, blood pressure, oxygen concentrations, hemoglobin concentrations, total hemoglobin concentration (tHb), saturation of peripheral oxygen ($SpO_2$), $SpO_2$ variability, regional oxygen saturation ($rSO_2$), apnea conditions, arrhythmia, and saturation pattern detection among other parameters and characteristics, including combinations and variations thereof. Physiological measurements can be performed using the various examples herein. Some of these include determining respiration rate from a finger, pulse rate from a finger, motion of patient, continuous non-invasive blood pressure measurement (CNIBP), deltaPOP (a measurement of the variability of the pleth pulses), variability of optical pleth to determine vessel elasticity, dehydration, apnea detection and monitoring, and auto-regulation of patients. In addition, enhancements to measurement include body location detection to determine where sensors are applied on patient, smart blood pressure cuffs, blood pressure measurement triggered when blood pressure changes beyond thresholds, enhanced cuff position and accuracy detection, and skin type and color detection. Also, the measurement systems described herein can provide various improvements to conventional optical pulse oximetry using optical signals separately or in tandem with electric field signals. Some examples include motion correction due to patient movement, sensor on/off tissue or finger, ECG lock for pleth signals, checking assumptions and correlations of optical-only measurements, reducing time to post results to a doctor or patient, correction of measurements for DC shifts, sensor pressure correction on tissue, signal quality improvements, sensor fault detection, optical signal fault detection, signal processing tailoring to skin/blood types and conditions, detecting and correcting changes in skin properties due to moisture/sweat or elasticity, improved signal analysis using wavelet analysis of signals, pleth morphology, or FFT (Fast Fourier Transform), and power saving by turning off optical sensors/emitters when not applied on tissue properly.

In yet further examples, the capacitance signal can be employed to reduce noise or enhance measurement of other non-optical physiological sensors. Breathing monitors can be coupled to a capacitive sensor on a fingertip, and motion of the patient as determined by the capacitive sensor can scale or modify the readings captured by the breathing monitors. The capacitance signal can be used to cross-check other physiological sensors. For example, if a first sensor observes a low breathing rate or lack of breathing, a capacitive signal can be monitored to determine if the breathing sensor is faulty or reading an actual low breathing rate event. In infant monitoring environments, such as a neonatal intensive care unit (NICU), breathing monitors can be difficult to apply and maintain proper positioning on a moving infant. Capacitance based sensors, as discussed herein, can monitor breathing or pulse rate of the infant to determine if the breathing as monitored by the breathing monitor is valid or if the sensor has fallen off or been mis-aligned. Furthermore, capacitance based sensing can be used to replace bulky breathing monitor equipment for infants and instead use only a small adhesive pad with a capacitive sensor or a clip-on sensor with a capacitive element. Capacitance sensing can be used in a NICU to monitor activity and movement, such as to ensure that an infant is moving regularly.

As a first example of a measurement system for measuring physiological parameters of a patient, FIG. 1A is presented. FIG. 1A is a system diagram illustrating measurement system 100. Elements of measurement system 100 measure one or more physiological parameters of tissue 140. In the example shown in FIG. 1A, measurement system 100 includes single plate capacitor 182 on a single side of tissue 140, using tissue 140 as a dielectric.

Measurement system 100 includes processing system 110, physiological sensor system 120, and capacitance system 130, with sensor node 190 and capacitance node 182 applied to tissue 140. Processing system 110 and physiological sensor system 120 communicate over link 170. Processing system 110 and capacitance system 130 communicate over link 171. Physiological sensor system 120 and sensor node 190 are coupled over link 160. Capacitance system 130 and capacitance node 182 are coupled over link 162. In some examples, processing system 110, physiological sensor system 120, and capacitance system 130 are included in measurement equipment 101. In addition to the capacitance and physiological sensors shown in FIG. 1A, measurement system 100 can also include further sensors, such as accelerometers, temperature sensors, moisture sensors, blood pressure cuffs, or other physiological and environmental sensors.

In operation, physiological sensor system 120 is configured to receive instructions and signals from processing system 110 over link 170. In some examples, physiological sensor system 120 is configured to perform signal detection and processing for signals received over link 160 and transfer information related to these signals to processing node 110 over link 170 for further processing and analysis. Physiological sensor system 120 can measure one or more physiological parameters of tissue 140 using sensor node 190. Physiological sensor system 120, along with sensor node 190, can comprise at least one of a pulse oximetry system, an ECG system, an acoustic physiological parameter measurement system, a breathing monitor, and a pulse rate monitor, among other physiological measurement systems, including combinations thereof. Physiological sensor system 120 or processing system 110 can also receive physiological parameters or other physiological information from other equipment and systems, such as other monitoring and detection equipment not shown in FIG. 1A. Capacitance system 130 is configured to receive instructions and signals from processing system 110 over link 171 to generate signals for emission as electric field signal 151. Capacitance system 130 is also configured to perform signal detection and processing for electric field signals monitored over link 162 and transfer information related to these signals to processing node 110 over link 171 for further processing and analysis.

Figure 1B:
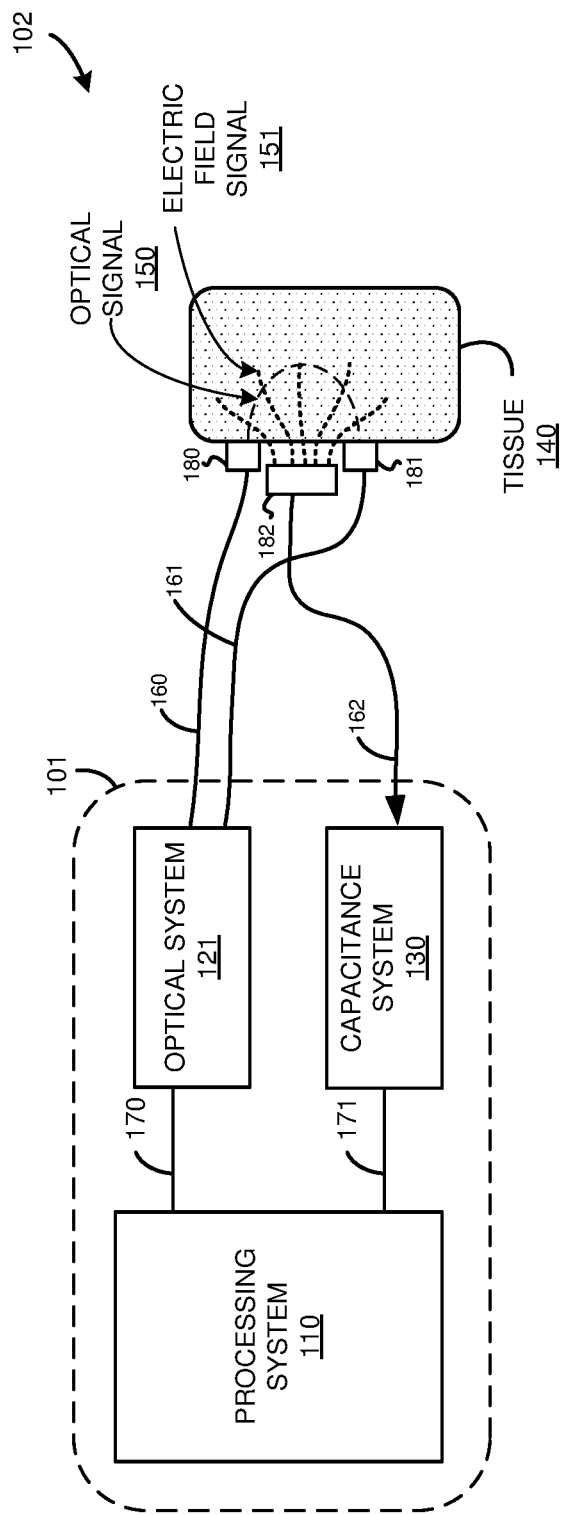
FIG. 1B is a system diagram illustrating a physiological measurement system.

In some examples, physiological sensor system 120 includes optical-based measurement equipment and systems. FIG. 1B is a system diagram illustrating an example configuration of measurement system 102. Elements of measurement system 102 in FIG. 1B emit and detect optical and electric field signals in tissue 140 of a patient for measuring one or more physiological parameters of tissue 140.

In the example shown in FIG. 1B, measurement system 102 includes a single plate capacitor positioned proximate to a single side of tissue 140. The single plate capacitor is included in capacitance node 180 in FIG. 1B. The single plate capacitor of capacitance node 180 can be placed on tissue 140 in some examples. However, in other examples, such as shown in FIG. 1B, the single plate capacitor of capacitance node 180 can have an air gap or have one or more layers of non-tissue material such as air, clothing, coatings, polymers, or other materials. Thus, in FIG. 1B, the single plate capacitor is in a non-contact configuration with regard to tissue 140. Also, the optical measurement system of FIG. 1B is shown as a reflectance pulse oximetry configuration with optical emitter and detector equipment positioned on a same side of tissue 140. Further examples can instead be employed, such as transmission pulse oximetry with optical emitter and detector equipment located on different sides of tissue 140.

Measurement system 102 includes processing system 110, optical system 121, and capacitance system 130, with optical nodes 180-181 and capacitance node 182 applied to tissue 140. Processing system 110 and optical system 121 communicate over link 170. Processing system 110 and capacitance system 130 communicate over link 171. Optical system 121 and optical node 180 are coupled over link 160. Optical system 121 and optical node 181 are coupled over link 161. Capacitance system 130 and capacitance node 182 are coupled over link 162. In some examples, processing system 110, optical system 121, and capacitance system 130 are included in measurement equipment 101. In addition to capacitance and optical sensors, measurement system 102 can also include further sensors, such as accelerometers, temperature sensors, moisture sensors, blood pressure cuffs, or other physiological and environmental sensors.

In operation, optical system 121 is configured to receive instructions and signals from processing system 110 over link 170 to generate signals for emission as optical signal 150. Optical system 121 is also configured to perform signal detection and processing for signals received over link 161 and transfer information related to these signals to processing node 110 over link 170 for further processing and analysis. Capacitance system 130 is configured to receive instructions and signals from processing system 110 over link 171 to generate signals for emission as electric field signal 151. Capacitance system 130 is also configured to perform signal detection and processing for electric field signals monitored over link 162 and transfer information related to these signals to processing node 110 over link 171 for further processing and analysis. Capacitance system 130 can measure a capacitance signal which is described below in FIG. 2.

As a first example operation of any of measurement systems 100 and 102, FIG. 2 is provided. FIG. 2 is a flow diagram illustrating a method of operation of a measurement system. The operations of FIG. 2 are referenced below parenthetically. In FIG. 2, physiological sensor system 120 detects (201) a physiological signal representative of one or more physiological parameters of a patient. As discussed in FIG. 1A, physiological sensor system 120 can comprise any of a pulse oximetry system, an ECG system, an acoustic physiological parameter measurement system, a breathing monitor, and a pulse rate monitor, among other physiological measurement systems, including combinations thereof. Thus, physiological sensor system 120 can measure physiological signals related to physiological parameters of tissue 140 using at least sensor node 190, or physiological sensor system 120 can monitor patient physiological parameters (in breathing monitor examples) to identify the physiological parameters.

Alternatively, physiological sensor system 120 can receive physiological parameters or other physiological information from other equipment and systems, such as external monitoring systems. In FIG. 2, a physiological parameter can be measured by another system not included in FIG. 1A, such as a capnometer, breathing rate measurement system, blood pressure system, pulse monitoring system, among others, including combinations thereof. Sensor system 120 can receive one or more physiological parameters from an external system instead of measuring signals related to physiological parameters.

Measurement system 102 of FIG. 1B illustrates an optical measurement configuration to detect physiological signals. FIG. 1B shows a pulse oximetry measurement system, namely optical system 121 and associated optical nodes 180-181. Optical system 121 emits signals over link 160 for emission as optical signal 150 into tissue 140, and optical node 180 emits optical signal 150 into tissue 140. In some examples, link 160 is a wired or wireless signal link, and carries a measurement signal to optical node 180 which converts the measurement signal into an optical signal and emits optical signal 150 into tissue 140. The optical signal can be emitted using a laser, laser diode, light emitting diode (LED), or other light emission device. In other examples, link 160 is an optical link, and carries an optical signal to optical node 180. Optical node 180 can comprise tissue interface optics, such as lenses, prisms, or other optical fiber-to-tissue optics, which interface optical link 160 to tissue 140 for emission of optical signal 150. One or more optical wavelengths can be used by optical node 180 to measure tissue 140, and the one or more optical wavelengths can be selected based on various physiological factors, such as isosbestic wavelengths associated with blood components of tissue 140. In a particular example, wavelengths such as 660 nm and 808 nm are employed.

Continuing in the pulse oximetry example of FIG. 1B, optical system 121 detects the optical signals after propagation through the tissue. Optical node 181 receives optical signal 150 after propagation through tissue 140. Optical system 121 receives signals over link 161 from optical node 181 representative of optical signal 150 after propagation through tissue 140. In some examples, link 161 is a wired or wireless signal link, and carries a detection signal from optical node 181 which converts a received optical signal 150 into a detection signal after detecting optical signal 150 from tissue 140. Optical signal 150 can be detected using a photodiode, avalanche photodiode, or other optical detection device, along with any associated tissue interface optics. In other examples, link 161 is an optical link, and carries an optical signal from optical node 181. Optical node 181 can comprise tissue interface optics, such as described above for node 180, which interface optical link 161 to tissue 140 for capture of optical signal 150 after propagation through tissue 140.

Capacitance system 130 applies (202) electric field signal 151 to tissue 140 to determine a capacitance signal. Capacitance system 130 generates one or more electric signals over link 162 to generate electric field signal 151 in tissue 140. Link 162 is an electric signal link which drives capacitance node 182 to emit electric field 151 in tissue 140. Electric field signal 151 can be applied by a capacitor portion of capacitance node 182. In some examples, capacitance node 182 includes a single plate capacitor which uses tissue 140 as a dielectric. Tissue interface elements, such as pads, adhesives, clamps, and the like, can be included in capacitance node 182. In many examples, electric field signal 151 is a modulated electric signal.

The capacitor portion, such as the single-plate capacitor employed in FIGS. 1A and 1B, can apply electric field 151 proximate to tissue 140, which can include application of electric field signal 151 without contact of any capacitor plate portion of capacitance node to tissue 140. In other examples, any associated capacitor plate portion of capacitance node 182 is positioned to contact tissue 140. A contact example is shown in FIG. 1A, while a non-contact example is shown in FIG. 1B. Electric field signal 151 can comprise a modulated signal produced by circuitry of capacitance system 130 and transferred onto link 162 for application of electric field signal 151 to tissue 140 by capacitance node 182.

Capacitance system 130 detects changes in electric field signal 151 to identify a capacitance signal. These changes in electric field signal 151 can be measured over link 162. The capacitance signal can correspond to a change in capacitance of a capacitor portion of capacitance node 182 that can be detected by capacitance system 130. The change in capacitance can be monitored as electric field signal 151 is applied to tissue and the capacitance signal can reflect the change in capacitance. Electric field signal 151 can comprise a modulated signal, such as a sine wave signal. Modulation circuitry used to produce electric field signal 151 can include a capacitor portion of capacitance node 182. Changes in a capacitance value of a capacitor used to apply electric field signal 151 to tissue can be detected by capacitance system 130 as a change in modulation frequency or a change in power draw of the capacitor or associated modulation circuitry, among other detection methods. These changes in electric field signal 151 can also be measured by monitoring changes in a noise level, current draw, or other characteristics of electric field signal 151 as detected by capacitance system 130. Capacitance system 130 can comprise capacitance-to-digital converter circuitry. The capacitance signal can be monitored concurrent with other physiological parameter monitoring, such as that described in operation 201.

Electric field signal 151 can experience changes due to a change in the dielectric environment into which electric field signal 151 is applied. The dielectric environment can include any materials that are proximate to a capacitor plate which applies electric field signal 151. Example materials in the dielectric environment include tissue 140, clothing, air gaps, pads, coatings, casings, gels, or adhesives, among other materials. The changes can be due to physiological changes in tissue 140 or changes in the physiological environment of tissue 140. The changes in electric field signal 151 can be caused by motion of tissue 140, where the motion is caused by venous blood movement within tissue 140, physical movement of tissue 140—such as movement of a limb associated with tissue 140, or due to changes in pressure/orientation of capacitance node 182 on tissue 140.

In further examples, tissue 140, or the associated patient, is connected electrically to an electrical reference potential, such as a ground potential. A low-resistance connection of tissue of the patient to the reference potential can be employed, such as a metallic bracelet worn by the patient, an electrical connection used for other physiological measurements, such as an ECG lead, or though tissue interface portions of system 100. The tissue interface portions can include clamp-on probes, adhesive pads, conductive foams, or conducting gels which interface electrically to tissue of the patient. The electrical grounding or reference potential connection can be employed to enhance signal measurement of the single-plate capacitor. Some measurements of the capacitance signal can be affected by unwanted influence from the environment around tissue 140, such as nearby objects, nearby people, things the patient is presently touching or contacting, among other influences. A reference or ground connection of tissue 140 or the associated patient can reduce unwanted noise and improve measurement signal amplitude.

Processing system 110 reduces (203) a noise level in the physiological signal based on at least the capacitance signal. In the example shown in FIG. 1B, an optical signal is measured which might include noise or undesired signal artifacts. Physiological parameters determined from the physiological signal might be inaccurate due to this noise. However, in this example, measured physiological signals can have various noise or undesired signal artifacts reduced or removed using the capacitance signal. For example, various signal elements of the capacitance signal can be isolated and used to remove unwanted noise from the physiological signals and determine physiological parameters. The physiological signals can include those identified in operation 201, such as by monitoring pulse oximetry-based physiological signals in FIG. 1B, among others. In one example, the capacitance signal can be monitored to detect motion associated with tissue 140. Signal elements of the capacitance signal due to motion of tissue 140 can be isolated and used to subtract unwanted motion-based noise artifacts from the pulse oximetry-based physiological signals. In examples where physiological parameters are received from external systems or equipment, processing system 110 can correct the physiological parameters using at least the capacitance signal to determine corrected physiological parameters of the patient.

In addition to correction of measured physiological signals using the capacitance signal, other enhanced measurements can be employed by measurement system 100. For example, measurement system 100 can provide enhanced measurement beyond the optical measurement of FIG. 1B due to the combination of optical and capacitance-based signals applied to tissue 140. These enhancements can compensate optical readings for variation due to movement of tissue 140, deformation of tissue 140, and pressure of sensor portions applied to tissue 140. In some examples, capacitance system 130 can detect when optical sensor portions, such as optical nodes 180-181 are or are not sufficiently applied to tissue 140. Responsive to optical nodes 180-181 not being sufficiently applied to tissue, measurement system 100 can suspend measurement of optical signal 150, prevent processing of optical signal 150 to determine physiological parameters, or alert an operator of measurement system 100 to an improper sensor application condition, among other operations. In other examples, a pressure-based compensation can be performed on optical signal 150 based on electric field signal 151 to provide more accurate and stable measurements of optical signal 150, as described below in FIG. 10.

In addition to capacitance system 130 being used to compensate for variability in optical signals in tissue 140, capacitance system 130 can be employed to add additional measurement capability to an optical-only measurement system. A pulse oximetry measurement to detect $SpO_2$ can be improved using capacitance system 130 and a single plate capacitor configuration, such as capacitance node 182. An optical-only hemoglobin measurement of blood of tissue 140 can be improved, or an optical or electrical plethysmograph can be measured, by adding a single plate capacitor configuration, such as capacitance node 182. A capacitive measurement can add additional measured parameters and can be employed in various hemoglobin and $SpO_2$ measurement methods to reduce a number of variables in associated blood parameter equations. For example, both optical and capacitive sensing can be used to reduce a number of unknown equation variables compared to an optical-only system. In some examples, respiratory rate of tissue 140 can be determined from heart rate changes detected using optical system 121 and capacitance system 130.

In another example, a multi-level measurement process can be employed. A high level of accuracy using both optical and capacitive measurements can be employed to measure physiological parameters of tissue 140, and a threshold condition can be established on one or more of the physiological parameters. If the threshold condition is not met, then a lower level of accuracy using only the capacitive measurements can be employed to monitor for the threshold condition. If the threshold condition is met during capacitive-only measurements, then optical system 121 can be engaged to provide the high level of accuracy for physiological measurement. As an example, a drop in oxygen saturation level is likely to trigger an increase in heart rate in a patient. A pulsatile signal indicative of heart rate can be detected from a capacitive measurement. Accordingly, a capacitive signal can be used to monitor heart rate while a pulse oximetry device is turned off to save power or reduce data collection requirements, without missing significant oxygen desaturation events. A pulse oximetry device can power down one or more emitters, such as LEDs, to save power. The capacitance signal can continue to track the heart rate and optionally cycle the LEDs on to confirm the heart rate and to check oxygen saturation. Examples of this multi-level measurement are discussed below regarding FIG. 11B. In further examples, automatic gain control elements of a measurement system can use a capacitance signal to track phases of cardiac cycles and adjust brightness of associated optical emitters to increase signal-to-noise characteristics during desired segments of the cardiac cycle.

In yet further examples, a reduction in time to post results to a doctor or patient can be achieved using capacitance-enhanced measurements. For example, a capacitance-based measurement of a physiological signal can be monitored which can give a doctor or patient a quick and rough estimate of a physiological parameter. If a more detailed or more accurate measurement is desired, then another measurement system, such as an optical system, can be enabled.

Figure 3:
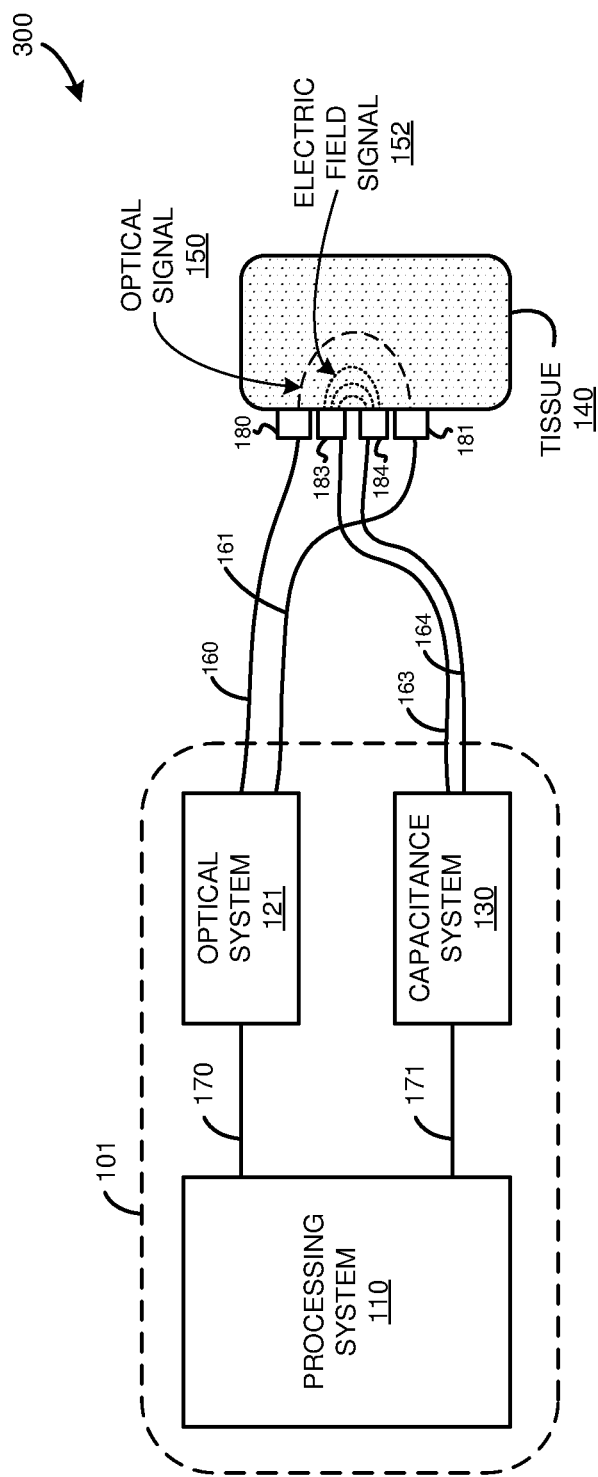
FIG. 3 is a system diagram illustrating a physiological measurement system.

Further examples of these various enhancements using capacitance-based measurements are described herein, such as in FIGS. 3-8. As a first example, FIG. 3 is a system diagram illustrating measurement system 300. Measurement system 300 includes at least capacitance nodes 183-184 and links 163-164. Measurement system 300 is also shown including some similar elements as found in FIGS. 1A and 1B, although variations are possible. It should be understood that other physiological measurement elements can be included in system 300. In FIG. 3, capacitance nodes 183-184 are shown located an exemplary distance apart. This distance can be established based on calibration of the capacitance signal to a specific spacing, among other spacing. In FIG. 3, a two-plate capacitor configuration is shown, with both capacitor plates located on the same side of tissue 140.

Measurement system 300 emits and detects optical and electric field signals in tissue 140 of a patient for measuring one or more physiological parameters of tissue 140. Measurement system 300 includes processing system 110, optical system 121, and capacitance system 130, with optical nodes 180-181 and capacitance nodes 183-184 applied to tissue 140. Processing system 110 and optical system 121 communicate over link 170. Processing system 110 and capacitance system 130 communicate over link 171. Optical system 121 and optical node 180 are coupled over link 160. Optical system 121 and optical node 181 are coupled over link 161. Capacitance system 130 and capacitance node 183 are coupled over link 163. Capacitance system 130 and capacitance node 184 are coupled over link 164. In some examples, processing system 110, optical system 121, and capacitance system 130 are included in measurement equipment 101.

In operation, optical system 121 is configured to receive instructions and signals from processing system 110 over link 170 to generate signals for emission as optical signal 150. Optical system 121 is also configured to perform signal detection and processing for signals received over link 161 and transfer information related to these signals to processing node 110 over link 170 for further processing and analysis. Capacitance system 130 is configured to receive instructions and signals from processing system 110 over link 171 to generate signals for emission as electric field signal 151. Capacitance system 130 is also configured to perform signal detection and processing for electric field signals monitored over links 163-164 and transfer information related to these signals to processing node 110 over link 171 for further processing and analysis.

Figure 4:
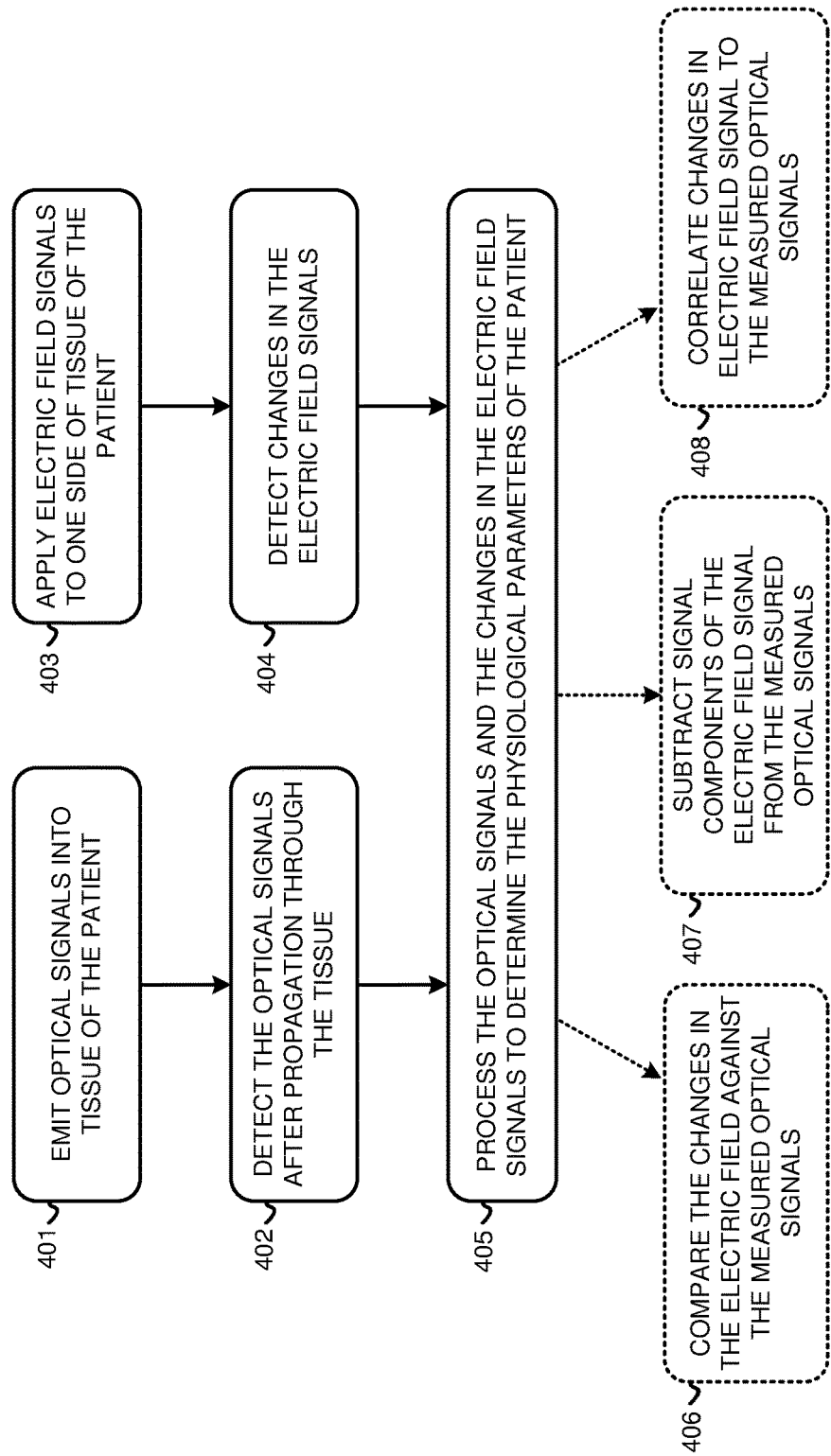
FIG. 4 is a flow diagram illustrating a method of operating a physiological measurement system.

As an example operation of measurement system 300, FIG. 4 is provided. FIG. 4 is a flow diagram illustrating a method of operation of measurement system 300. The operations of FIG. 4 are referenced below parenthetically. In FIG. 4, optical system 121 emits (401) optical signal 150 into tissue 140 of the patient. Optical system 121 emits signals over link 160 for emission as at least optical signal 150 into tissue 140, and optical node 180 emits optical signal 150 into tissue 140. In some examples, link 160 is an electric signal link, and carries an electrical signal to optical node 180 which converts the electrical signal into an optical signal and emits optical signal 150 into tissue 140. The optical signal can be emitted using a laser, laser diode, light emitting diode (LED), or other light emission device. In other examples, link 160 is an optical link, and carries an optical signal to optical node 180. Optical node 180 can comprise tissue interface optics which interface optical link 160 to tissue 140 for emission of optical signal 150.

Optical system 121 detects (402) the optical signals after propagation through the tissue. Optical node 181 receives optical signal 150 after propagation through tissue 140. Optical system 121 receives signals over link 161 from optical node 181 representative of optical signal 150 after propagation through tissue 140. In some examples, link 161 is an electric signal link, and carries an electrical signal from optical node 181 which converts a received optical signal 150 into an electrical signal after detecting optical signal 150 in tissue 140. Optical signal 150 can be detected using a photodiode, avalanche photodiode, or other optical detection device, along with any associated tissue interface optics. In other examples, link 161 is an optical link, and carries an optical signal from optical node 181. Optical node 181 can comprise tissue interface optics which interface optical link 161 to tissue 140 for capture of optical signal 150 after propagation through tissue 140.

Capacitance system 130 applies (403) electric field signal 152 to tissue 140. Capacitance system 130 generates one or more electric signals over links 163-164 to generate electric field signal 152 in tissue 140. Links 163-164 are electric signal links which drive capacitance nodes 183-184 to emit electric field 152 in tissue 140. In this example, capacitance nodes 183-184 form a two-plate capacitor positioned on a single side of tissue 140, and uses tissue 140 as a dielectric. Tissue interface elements can be included in capacitance nodes 183-184. In many examples, electric field signal 152 is a modulated electric signal.

Capacitance system 130 detects (404) changes in electric field signal 152. Capacitance system 130 measures changes in electric field signal 152 over links 163-164. As the environment of tissue 140, the internals of tissue 140, and tissue 140 itself changes, associated changes in electric field signal 152 can be monitored by capacitance system 130. These changes can be reflected in a change in capacitance of a capacitor formed by capacitance nodes 183-184. In some examples, the changes in electric field signal 152 are due to motion of tissue 140, where the motion is caused by venous blood movement within tissue 140, physical movement of tissue 140, such as movement of a limb associated with tissue 140, or due to pressure/orientation of capacitance nodes 183-184 on tissue 140. In further examples, the changes in electric field signal 152 are due to changes in a capacitance value associated with capacitance nodes 183-184 due to variation in the dielectric environment of capacitance nodes 183-184. These changes can also be changes in a noise level, current draw, power level, or other characteristics of electric field signal 152 as detected by capacitance system 130.

Processing system 110 processes (405) optical signal 150 and the changes in electric field signal 152 to determine the physiological parameters of the patient. In some examples, processing the changes in electric field signal 152 includes detecting motion or noise induced by tissue 140, such as by motion of tissue 140, motion of biological elements within tissue 140, environmental noise, signal noise, or other effects. These effects can be processed to correct for noise or motion artifacts of optical signal 150 to determine physiological parameters.

The processing performed in operation 405 can include different processing techniques. In a first example, processing system 110 compares (406) changes in electric field signal 152 against measured optical signal 150 to determine the physiological parameters. For example, signal components of electric field signal 152 can be compared to signal components of measured optical signal 150 to improve measured optical signal 150 and determine physiological parameters from the improved optical signal 150. A capacitance signal or changes in electric field signal 152 can be used to identify noise in a portion of measured optical signal 150, and then that portion can be de-weighted when processing measured optical signal 150 to determine a physiological parameter. A capacitance signal or changes in electric field signal 152 can be used to identify a period of noise in the capacitance signal or the changes in electric field signal 152, and this period of noise can be used to drop or exclude a correlating timewise portion of measured optical signal 150 during processing to determine any physiological parameters. Thus, noisy periods or portions of measured optical signal 150 can be excluded from calculation of physiological parameters.

In a second example, processing system 110 subtracts (407) signal components of electric field signal 152 from measured optical signal 150 to determine the physiological parameters. For example, signal components of electric field signal 152 can be subtracted from signal components of measured optical signal 150 to reduce noise in measured optical signal 150 and determine physiological parameters from the noise-reduced optical signal 150. A scaled or filtered portion of a capacitance signal or changes in electric field signal 152 can be subtracted from a correlated portion of measured optical signal 150.

In a third example, processing system correlates (408) changes in electric field signal 152 to measured optical signal 150 to determine the physiological parameters. For example, signal components of electric field signal 152 can be correlated to signal components of measured optical signal 150 to improve measured optical signal 150 and determine physiological parameters from the improved optical signal 150. Other processing techniques can be employed, such as those discussed herein, including combinations and variations thereof.

Measurement system 300 can provide enhanced measurement beyond optical measurement due to at least the combination of optical and capacitance-based signals applied to tissue 140. These enhancements can compensate optical readings for variables in movement of tissue 140, deformation of tissue 140, and pressure of sensor portions applied to tissue 140. In some examples, capacitance system 130 can detect when optical sensor portions, such as optical nodes 180-181 are sufficiently applied to tissue 140. Responsive to optical nodes 180-181 not being sufficiently applied to tissue, measurement system 100 can prevent measurement by optical signal 150 or prevent processing of at least optical signal 150 to determine physiological parameters. In other examples, a pressure-based compensation can be performed on optical signal 150 based on electric field signal 151 to provide more accurate and stable measurements of optical signal 150.

In addition to capacitance system 130 being used to identify and compensate for variability in the detected optical signals, capacitance system 130 can be employed to add additional measurement capability to an optical measurement system. A pulse oximetry measurement to detect $SpO_2$ can be improved using capacitance system 130 and a dual-plate, single-sided capacitor configuration, such as capacitance nodes 183-184. An optical hemoglobin measurement of blood of tissue 140 can be improved, or an optical or electrical plethysmograph can be measured, by adding a dual-plate, single-sided capacitor configuration, such as capacitance nodes 183-184. In some examples, respiratory rate of tissue 140 can be determined from heart rate changes detected using optical system 121 and capacitance system 130.

Figure 5:
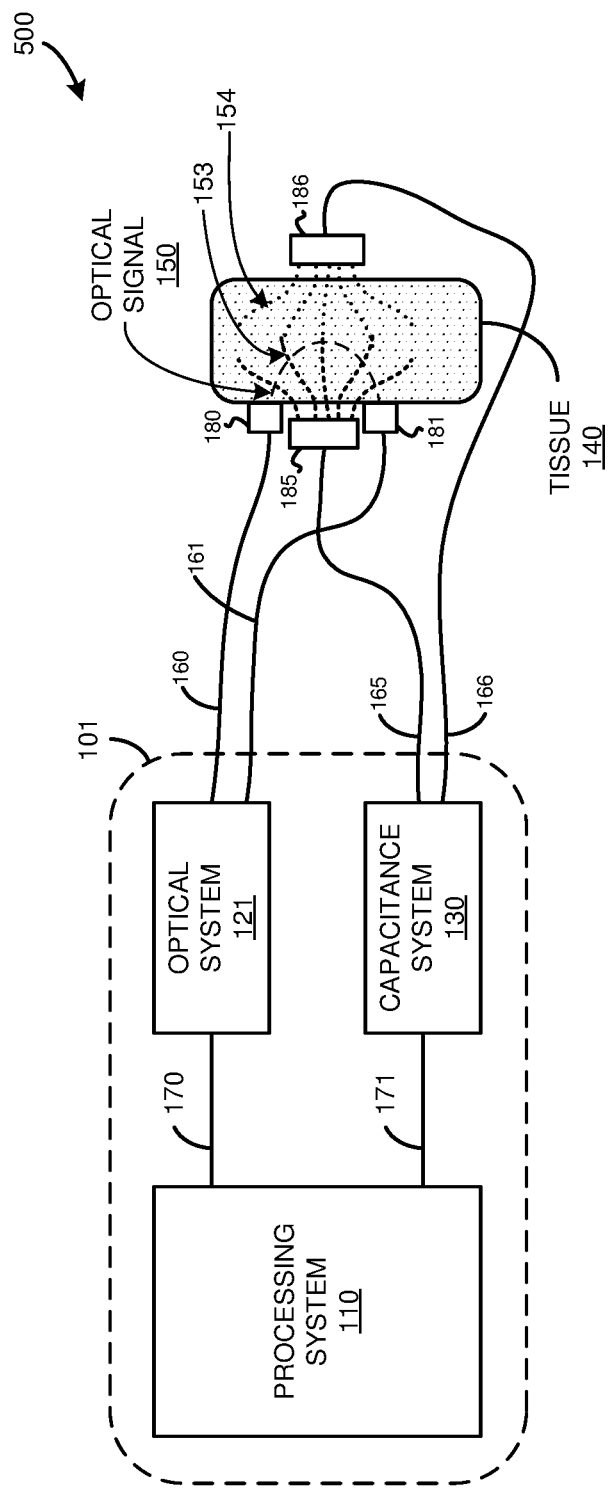
FIG. 5 is a system diagram illustrating a physiological measurement system.

Further examples of these various enhancements using capacitance-based measurements are described herein, such as in FIG. 5. FIG. 5 is a system diagram illustrating measurement system 500. Measurement system 500 includes at least capacitance nodes 185-186 and links 165-166. Measurement system 500 is also shown including some similar elements as found in FIGS. 1A and 1B, although variations are possible. It should be understood that other physiological measurement systems can be included in system 500. FIG. 5 includes two single-plate capacitors, with each single plate capacitor positioned on a single side of tissue 140. Also, each single plate capacitor can be applied onto tissue 140, or can include an air gap and other materials that separate each single plate capacitor from tissue 140. FIG. 5 shows an exemplary gap between tissue 140 and each single plate capacitor.

Measurement system 500 emits and detects optical and electric field signals in tissue 140 of a patient for measuring one or more physiological parameters of tissue 140. Measurement system 500 includes processing system 110, optical system 121, and capacitance system 130, with optical nodes 180-181 and capacitance nodes 185-186 applied to tissue 140. Processing system 110 and optical system 121 communicate over link 170. Processing system 110 and capacitance system 130 communicate over link 171. Optical system 121 and optical node 180 are coupled over link 160. Optical system 121 and optical node 181 are coupled over link 161. Capacitance system 130 and capacitance node 185 are coupled over link 165. Capacitance system 130 and capacitance node 186 are coupled over link 166. In some examples, processing system 110, optical system 121, and capacitance system 130 are included in measurement equipment 101.

In operation, optical system 121 is configured to receive instructions and signals from processing system 110 over link 170 to generate signals for emission as optical signal 150. Optical system 121 is also configured to perform signal detection and processing for signals received over link 161 and transfer information related to these signals to processing node 110 over link 170 for further processing and analysis. Capacitance system 130 is configured to receive instructions and signals from processing system 110 over link 171 to generate signals for emission as electric field signals 153-154. Capacitance system 130 is also configured to perform signal detection and processing for electric field signals monitored over links 165-166 and transfer information related to these signals to processing node 110 over link 171 for further processing and analysis.

Figure 6:
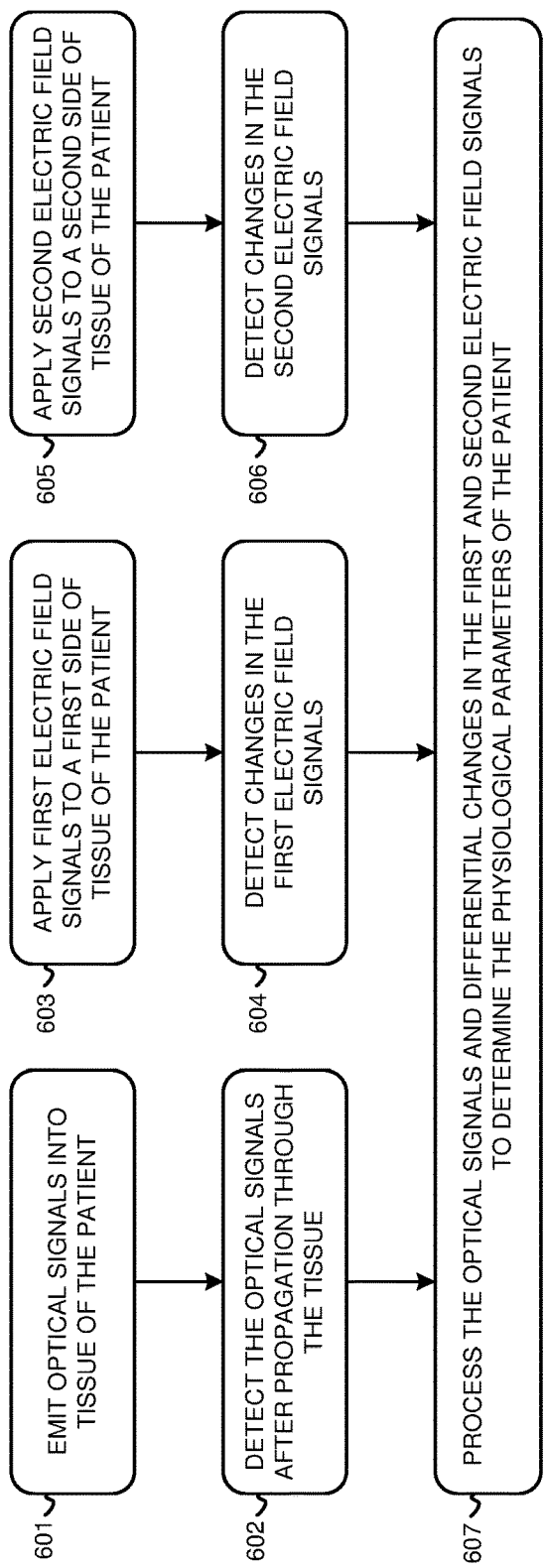
FIG. 6 is a flow diagram illustrating a method of operating a physiological measurement system.

As an example operation of measurement system 500, FIG. 6 is provided. FIG. 6 is a flow diagram illustrating a method of operation of measurement system 500. The operations of FIG. 6 are referenced below parenthetically. In FIG. 6, optical system 121 emits (601) optical signal 150 into tissue 140 of the patient. Optical system 121 emits signals over link 160 for emission as optical signal 150 into tissue 140, and optical node 180 emits optical signal 150 into tissue 140. In some examples, link 160 is an electric signal link, and carries an electrical signal to optical node 180 which converts the electrical signal into an optical signal and emits optical signal 150 into tissue 140. The optical signal can be emitted using a laser, laser diode, light emitting diode (LED), or other light emission device. In other examples, link 160 is an optical link, and carries an optical signal to optical node 180. Optical node 180 can comprise tissue interface optics which interface optical link 160 to tissue 140 for emission of optical signal 150.

Optical system 121 detects (602) the optical signals after propagation through the tissue. Optical node 181 receives optical signal 150 after propagation through tissue 140. Optical system 121 receives signals over link 161 from optical node 181 representative of optical signal 150 after propagation through tissue 140. In some examples, link 161 is an electric signal link, and carries an electrical signal from optical node 181 which converts a received optical signal 150 into an electrical signal after detecting optical signal 150 in tissue 140. Optical signal 150 can be detected using a photodiode, avalanche photodiode, or other optical detection device, along with any associated tissue interface optics. In other examples, link 161 is an optical link, and carries an optical signal from optical node 181. Optical node 181 can comprise tissue interface optics which interface optical link 161 to tissue 140 for capture of optical signal 150 after propagation through tissue 140.

Capacitance system 130 applies (603) a first electric field as electric field signal 153 to tissue 140. Capacitance system 130 generates one or more electric signals over link 165 to generate electric field signal 153 in tissue 140. Link 165 is an electric signal link which drives capacitance node 185 to emit electric field 153 in tissue 140. In this example, capacitance node 185 forms a single-plate capacitor positioned on a single side of tissue 140, and uses tissue 140 as a dielectric. Tissue interface elements can be included in capacitance node 185. In many examples, electric field signal 153 is generated by a modulated electric signal.

Capacitance system 130 detects (604) changes in electric field signal 153. Capacitance system 130 measures changes in electric field signal 153 over link 165. As the environment of tissue 140, the internals of tissue 140, and tissue 140 itself changes, associated changes in electric field signal 153 can be monitored by capacitance system 130. In some examples, the changes in electric field signal 153 are due to motion of tissue 140, where the motion is caused by venous blood movement within tissue 140, physical movement of tissue 140, such as movement of a limb associated with tissue 140, or due to pressure/orientation of capacitance node 185 on tissue 140. In further examples, the changes in electric field signal 153 are due to changes in a capacitance value associated with capacitance node 185 due to variation in the dielectric environment of capacitance node 185. These changes can also be changes in a noise level, current draw, power level, or other characteristics of electric field signal 153 as detected by capacitance system 130.

Capacitance system 130 applies (605) a second electric field as electric field signal 154 to tissue 140. Capacitance system 130 generates one or more electric signals over link 166 to generate electric field signal 154 in tissue 140. Link 166 is an electric signal link which drives capacitance node 186 to emit electric field 154 in tissue 140. In this example, capacitance node 186 forms a single-plate capacitor positioned on a single side of tissue 140, and uses tissue 140 as a dielectric. Capacitance node 186 is positioned on a different side of tissue 140 than capacitance node 185. In some examples, each of capacitance nodes 185-186 are positioned on opposite sides of tissue 140, such as a top and bottom of a finger or digit. In other examples, each of capacitance nodes 185-186 are positioned on adjacent sides of tissue 140, such as a top and adjacent side of a finger or digit. Tissue interface elements can be included in capacitance node 186. In many examples, electric field signal 154 is a modulated electric signal.

In some examples, capacitance system 130 is configured to emit electric field signal 153 and electric field signal 154 simultaneously, using each of capacitance node 185 and capacitance node 186 as separate single-plate capacitors. Single-plate operation can be achieved in some examples by using isolation circuitry, such as separate measurement and drive circuitry, transformers, opto-isolators, or other isolation elements to ensure single-plate operation. When simultaneous operation is performed, each of capacitance node 185 and capacitance node 186 can use similar or different modulation frequencies for the respective electric field signals. For example, non-interfering modulation frequencies can be selected for each of electric field signal 153 and electric field signal 154. Frequency hopping, chirping, or spread spectrum techniques can also be employed to minimize interference of simultaneous measurement using electric field signal 153 and electric field signal 154. In further examples, the modulation frequency can be swapped after a first measurement is taken to perform a second measurement using simultaneous electric field signal 153 and electric field signal 154. In yet further examples, the modulation frequency of an associated electric field signal can be selected to minimize interference with other measurement devices, such as other physiological measurement equipment monitoring the patient. Non-simultaneous emission of electric field signal 153 and electric field signal 154 can also be employed, such as when using a similar modulation frequency for each of electric field signal 153 and electric field signal 154. For example, a sequential measurement using electric field signal 153 and electric field signal 154 can be employed.

Capacitance system 130 detects (606) changes in electric field signal 154. Capacitance system 130 measures changes in electric field signal 154 over link 166. As the environment of tissue 140, the internals of tissue 140, and tissue 140 itself changes, associated changes in electric field signal 154 can be monitored by capacitance system 130. These changes can be reflected in a change in capacitance of a capacitor formed by capacitance node 186 due to changes in the dielectric environment of capacitance node 186. The change in capacitance can be reflected in a capacitance signal monitored by capacitance system 130. In some examples, the changes in electric field signal 154 are due to motion of tissue 140, where the motion is caused by venous blood movement within tissue 140, physical movement of tissue 140, such as movement of a limb associated with tissue 140, or due to pressure/orientation of capacitance node 186 on tissue 140. In further examples, the changes in electric field signal 154 are due to changes in a capacitance value associated with capacitance node 186 due to variation in the dielectric environment of capacitance node 186. These changes can also be changes in a noise level, current draw, power level, or other characteristics of electric field signal 154 as detected by capacitance system 130.

Processing system 110 processes (607) optical signal 150, the changes in first electric field signal 153, and changes in second electric field signal 154 to determine the physiological parameters of the patient. In some examples, processing the changes in electric field signals 153-154 includes detecting motion or noise induced by tissue 140, such as by motion of tissue 140, motion of biological elements within tissue 140, environmental noise, signal noise, or other effects. These effects can be used to correct for noise or motion artifacts of optical signal 150 to determine the physiological parameters. The processing performed in operation 607 can include different processing techniques, such as those described in FIG. 4.

Figure 7:
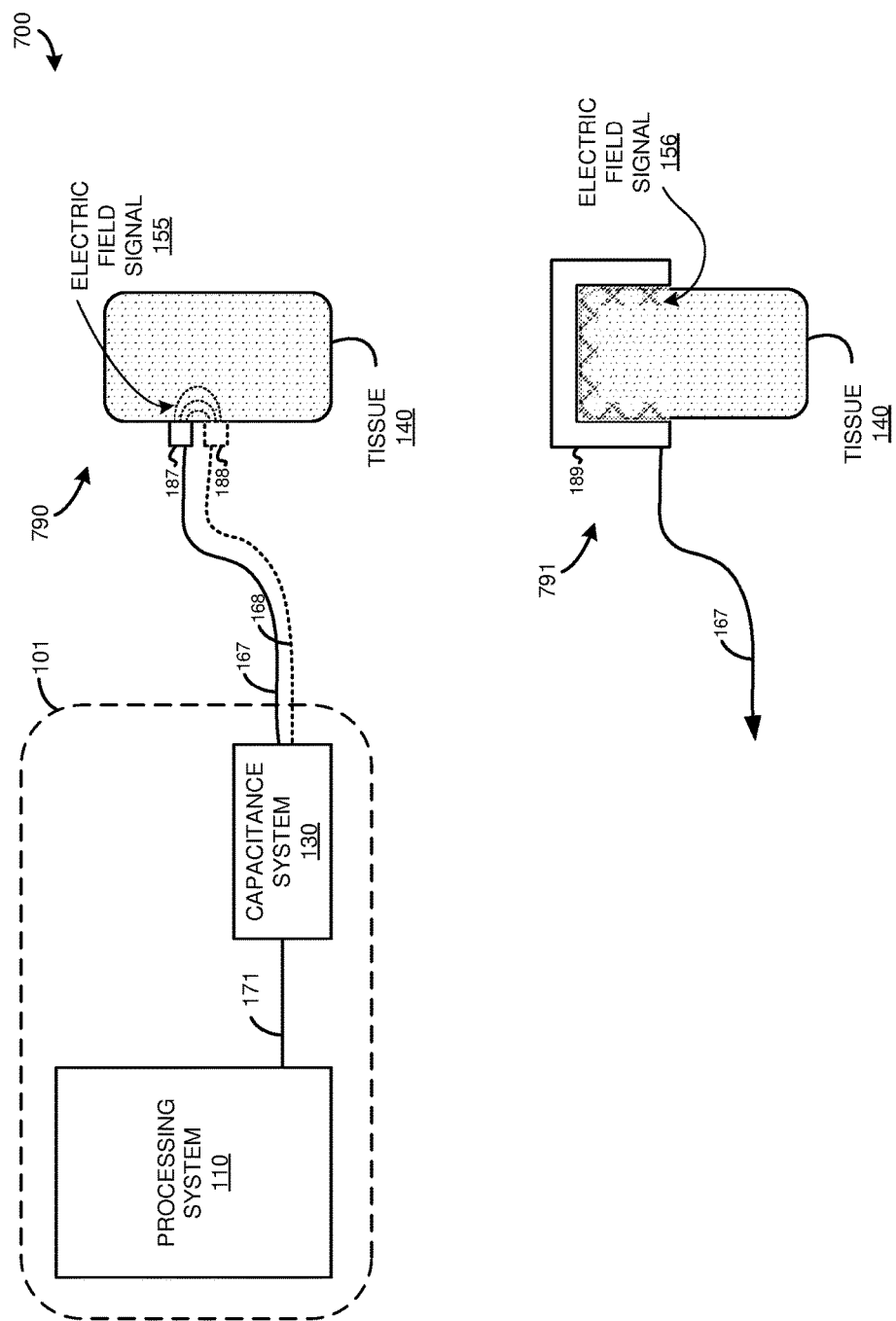
FIG. 7 is a system diagram illustrating a physiological measurement system.

Further examples of these various enhancements using capacitance-based measurements are described herein, such as in FIG. 7. FIG. 7 is a system diagram illustrating measurement system 700. Measurement system 700 is also shown including some similar elements as found in FIGS. 1A and 1B, although variations are possible. Measurement system 700 also omits optical measurement elements as discussed in the previous examples. It should be understood that other physiological measurement systems can be included in system 700.

FIG. 7 shows two example capacitor arrangements, namely arrangement 790 and 791. Capacitor arrangement 790 illustrates one or more capacitance nodes 187-188 positioned on the same side of tissue 140. In a first example of arrangement 790, a single plate capacitor of capacitance node 187 is employed on a single side of tissue 140. In a second example of arrangement 790, a two-plate capacitor is employed via capacitance nodes 187-188—with both capacitor plates of the two-plate capacitor positioned on a single side of tissue 140. Capacitor arrangement 791 illustrates a single plate capacitor of capacitance node 189 that wraps around tissue 140. Capacitance node 189 can comprise a rigid or flexible material to achieve the wrap-around feature illustrated in FIG. 7. In some examples, capacitor plates associated with capacitance nodes 187-189 are positioned on tissue 140, while in other examples, an air gap or other material separates the associated capacitor plates from tissue 140.

Measurement system 700 emits and detects electric field signals in tissue 140 of a patient for measuring one or more physiological parameters of tissue 140. Measurement system 700 includes processing system 110 and capacitance system 130, with capacitance nodes 187-189 applied to tissue 140. Processing system 110 and capacitance system 130 communicate over link 171. Capacitance system 130 and capacitance node 187 are coupled over link 167. Alternatively, capacitance system 130 and capacitance node 189 are coupled over link 167. Capacitance system 130 and optional capacitance node 188 are coupled over link 168. In some examples, processing system 110 and capacitance system 130 are included in measurement equipment 101. Capacitance nodes 187-188 are shown as located an exemplary distance apart. This distance can be arbitrary, or can be established based on calibration of the capacitance signal to a specific spacing, among other spacing.

In operation, capacitance system 130 is configured to receive instructions and signals from processing system 110 over link 171 to generate signals for emission as electric field signal 155. Alternatively, capacitance system 130 can be configured to receive instructions and signals from processing system 110 over link 171 to generate signals for emission as electric field signal 156. Capacitance system 130 is also configured to perform signal detection and processing for electric field signals monitored over links 167-168 and transfer information related to these signals to processing node 110 over link 171 for further processing and analysis.

In further examples, one or more portions of measurement system 700 can be incorporated into a wearable device. For example, at least capacitance node 187 can be incorporated into a fitness wristband for monitoring of physiological parameters during fitness activities. This fitness wristband can include moisture and sweat protection to isolate elements of measurement system 700 from environmental exposure. Capacitance measurements for fitness can include breathing rate, heart rate, sweat levels, electrolyte loss rate, running pace, and changes thereto. In some examples, all elements of measurement system 700 are included in the fitness wristband, with capacitance node 187 configured to be located next to tissue of the fitness participant when worn, such as contacting skin of a wearer. It should be understood that one capacitor plate (such as capacitance node 187 or 189) or two capacitor plates (such as capacitance nodes 187-188) can be incorporated into the fitness wristband, as discussed above FIG. 7 and below for FIG. 8. In some examples, such as in capacitor arrangement 791, a flexible or bendable capacitor plate can be employed.

Figure 8:
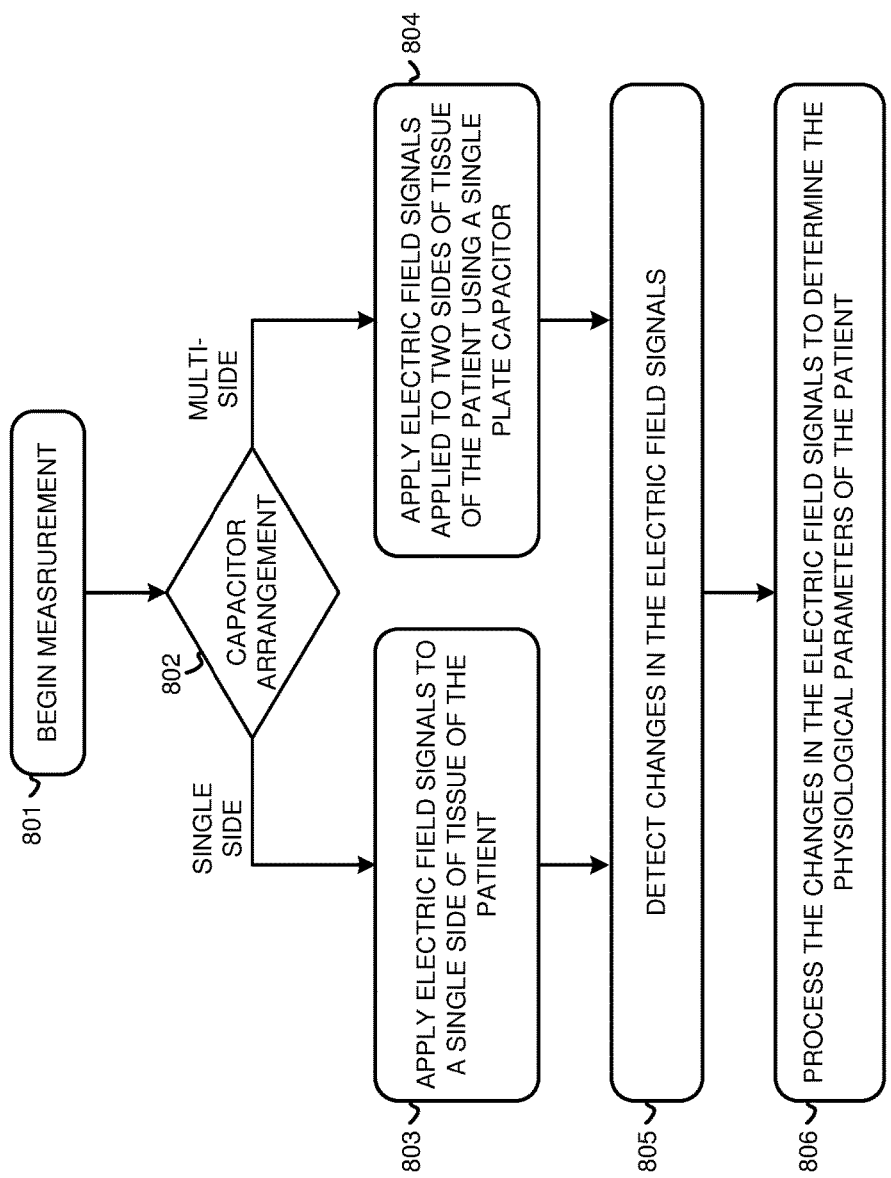
FIG. 8 is a flow diagram illustrating a method of operating a physiological measurement system.

As an example operation of measurement system 700, FIG. 8 is provided. FIG. 8 is a flow diagram illustrating a method of operation of measurement system 700. The operations of FIG. 8 are referenced below parenthetically. In FIG. 8, a physiological measurement begins (801) and a selection of measurement style is selected based on a capacitor plate arrangement (802). In first capacitor plate arrangement, such as illustrated in arrangement 790, one or more capacitor plates are positioned on a single side of tissue 140. In a second capacitor plate arrangement, such as illustrated by arrangement 791, a single capacitor plate is positioned on more than one side of tissue 140, such as by wrapping around a finger or limb of a patient. Tissue interface elements can be included in capacitance nodes 187-189, such as adhesives, clamps, pads, gels, and the like.

If a single side arrangement 790 is employed, capacitance system 130 applies (803) applies at least electric field signal 155 to a single side of tissue 140 of the patient. Capacitance system 130 generates one or more electric signals over link 167 and optionally link 168 to generate electric field signal 155 in tissue 140. Links 167-168 are each electric signal links which drives associated capacitance nodes 187-188 to emit electric field 155 in tissue 140. In a first example, capacitance node 187 is employed and capacitance node 188 is omitted. When only capacitance node 187 is employed, capacitance node 187 forms a single plate capacitor to emit electric field signal 155 into tissue 140. In a second example, both capacitance node 187 and capacitance node 188 are employed. When both capacitance nodes 187-188 are employed, capacitance nodes 187-188 comprise a two-plate capacitor applied to the same side of tissue 140. Capacitance nodes 187-188 can use tissue 140 as a dielectric. In many examples, electric field signal 155 is a modulated signal.

If a multi-side arrangement 791 is employed, capacitance system 130 applies (804) applies at least electric field signal 156 to more than one side of tissue 140 of the patient. Capacitance system 130 generates one or more electric signals over link 167 to generate electric field signal 156 in tissue 140. Capacitance node 189 forms a single plate capacitor to emit electric field signal 156 into tissue 140. Capacitance node 189 can use tissue 140 as a dielectric, as well as any associated air gaps or other materials. In many examples, electric field signal 156 is a modulated signal.

Capacitance system 130 detects (805) changes in electric field signal 155, or alternatively electric field signal 156. Capacitance system 130 measures changes in electric field signal 155/156 over one or more of links 167-168. As the environment of tissue 140, the internals of tissue 140, and tissue 140 itself changes, associated changes in electric field signal 155/156 can be monitored by capacitance system 130. These changes can be reflected in a change in capacitance of a capacitor formed by one or more of capacitance nodes 187-189 due to changes in the dielectric environment of an associated capacitance node 187-189. These changes can be changes in a noise level, current draw, power level, or other characteristics of electric field signal 155/156 as detected by capacitance system 130.

Processing system 110 processes (806) the changes in electric field signal 155 to determine the physiological parameters of the patient. In this example, the physiological parameter identified is a hemoglobin concentration of blood in tissue 140 of the patent. The hemoglobin concentration is measured using a single plate capacitor when capacitance node 187 or 189 are employed alone, or using a two-plate single-side capacitor when both capacitance nodes 187-188 are employed. Further physiological parameters can be measured, such as ECG information. The processing performed in operation 806 can include different processing techniques, such as those described in FIG. 4.

Returning back to the elements of FIGS. 1-8, processing system 110 comprises communication interfaces, computer systems, microprocessors, circuitry, non-transient computer-readable media, or other processing devices or software systems, and may be distributed among multiple processing devices. Processing system 110 can be included in the equipment or systems of optical system 121 or capacitance system 130, or can be included in separate equipment or systems. Examples of processing system 110 may also include software such as an operating system, logs, utilities, drivers, databases, data structures, processing algorithms, networking software, and other software stored on non-transient computer-readable media.

Physiological sensor system 120 can comprise at least one of a pulse oximetry system, an ECG system, an acoustic physiological parameter measurement system, a breathing monitor, a blood pressure monitoring system, and a pulse rate monitor, among other physiological measurement systems, including combinations thereof. Physiological sensor system 120 can also receive physiological parameters or other physiological information from other equipment and systems, such as other monitoring and detection equipment not shown. For example, a separate monitoring device can be employed and live physiological data can be transferred by the separate monitoring device for receipt by physiological sensor system 120. Physiological sensor system 120 can comprise transceivers, network interfaces, data links, and the like to receive this physiological data from the separate monitoring equipment. In another example, physiological sensor system 120 can instead monitor the physiological parameters itself, and include the associated monitoring equipment mentioned above. In further examples, physiological sensor system 120 can comprise environmental sensing equipment and systems, such as temperature sensing equipment, accelerometers, clocks, timers, chemical sensors, pressure sensors, or other sensing equipment to supplement patient monitoring equipment.

Optical system 121 can include electrical to optical conversion circuitry and equipment, optical modulation equipment, and optical waveguide interface equipment. Optical system 121 can include direct digital synthesis (DDS) components, CD/DVD laser driver components, function generators, oscillators, or other signal generation components, filters, delay elements, signal conditioning components, such as passive signal conditioning devices, attenuators, filters, and directional couplers, active signal conditioning devices, amplifiers, or frequency converters, including combinations thereof. Optical system 121 can also include switching, multiplexing, or buffering circuitry, such as solid-state switches, RF switches, diodes, or other solid state devices. Optical system 121 also can include laser elements such as a laser diode, solid-state laser, or other laser device, along with associated driving circuitry. Optical couplers, cabling, or attachments can be included to optically mate to links 160-161. Optical system 121 can also include light detection equipment, optical to electrical conversion circuitry, photon density wave characteristic detection equipment, and analog-to-digital conversion equipment. Optical system 121 can include one or more photodiodes, phototransistors, avalanche photodiodes (APD), or other optoelectronic sensors, along with associated receiver circuitry such as amplifiers or filters. Optical system 121 can also include phase and amplitude detection circuitry and processing elements.

Capacitance system 130 can comprise modulation circuitry, digital to analog conversion circuitry, analog to digital conversion circuitry, capacitor to digital conversion circuitry, amplifiers, impedance matching circuitry, analog switches, transceivers, processing circuitry, and other circuitry, including combinations thereof. Capacitance system 130 receives instructions from processing system 110 to drive electric field signals in tissue. Capacitance system 130 detects electric field properties of tissue and the environment around a patient and sensor equipment, as monitored by associated capacitance nodes. Capacitance system 130 can process the electric field properties from an analog format to a digital format for transfer to processing system 110. In some examples, capacitance system 130 comprises a capacitance detector, which can detect changes in capacitance of associated capacitance nodes. Capacitance system 130 can include capacitance measurement components such as Analog Devices AD7745. Capacitance system 130 can include touch screen controllers or associated integrated processing devices, such as Kinetis K10 devices (Freescale Semiconductor, Inc.).

Tissue 140 illustrates a portion of the tissue of a patient undergoing measurement of a physiological parameter, and is represented by a rectangular element for simplicity in FIGS. 1, 3, 5, and 7. It should be understood that tissue 140 can represent a finger, fingertip, toe, earlobe, chest, foot, arm, leg, head, limb, forehead, or other tissue portion of a patient undergoing physiological parameter measurement. Tissue 140 can comprise muscle, fat, blood, vessels, bone, or other tissue components. The blood portion of tissue 140 can include tissue diffuse blood and arterial or venous blood. In some examples, tissue 140 is instead a test sample or representative material for calibration or testing of system 100. The patient undergoing measurement can be any individual organism or group or organisms.

Links 160-161 can comprise optical links, wired electrical links, or wireless links. In examples where ones of links 160-161 comprise optical links, links 160-161 each comprise one or more optical waveguides, and use glass, polymer, air, space, or some other material as the transport media for transmission of light, and can each include multimode fiber (MMF) or single mode fiber (SMF) materials. A sheath or loom can be employed to bundle each of links 160-161 together for convenience. One end of each of links 160-161 mates with an associated component of optical system 121, and the other end of each of links 160-161 is configured to interface with tissue 140 through an associated optical node 180-181. Link 160 is configured to emit light via optical node 180 into tissue 140, while link 161 is configured to receive light via optical node 181 from tissue 140. Also, in examples where links 160-161 comprise optical links, optical nodes 180-181 can comprise one or more optical interfacing elements to interface the waveguide portions of links 160-161 to tissue 140. In examples where ones of links 160-161 comprise wired electrical links, links 160-161 each comprise one or more wired for carrying electrical to and from ones of optical nodes 180-181. In examples where ones of links 160-161 comprise wireless links, links 160-161 can include wireless signaling for exchanging communications between optical nodes 180-181 and optical system 121.

Optical node 180 can comprise can include laser elements such as a laser diodes, solid-state lasers, light emitting diodes (LED), or other light emitting devices, along with associated driving circuitry and electrical-to-optical conversion circuitry. Optical node 181 can include light detection equipment, optical to electrical conversion circuitry, photon density wave characteristic detection equipment, and analog-to-digital conversion equipment. Optical node 181 can include one or more photodiodes, phototransistors, avalanche photodiodes (APD), or other optoelectronic sensors, along with associated receiver circuitry such as amplifiers or filters. Optical couplers, cabling, lenses, prisms, or attachments can be included in optical nodes 180-181 to optically mate tissue 140 to links 160-161. In examples where links 160-161 are wireless links, optical nodes 180-181 can include wireless transceivers and antennas.

In FIGS. 1, 3, 5, and 7, link 160 and link 161 are shown coupled to optical nodes 180 and 181 which are located an exemplary distance apart, but can be located on the surface of tissue 140 at predetermined locations or distances. Although the term 'optical' is used herein for convenience, it should be understood that the optical measurement signals are not limited to visible light, and can comprise any light wavelength, such as visible, infrared, ultraviolet, or other signals.

Capacitance links 162-168 each comprise one or more electrical links for emitting or detecting an electric field in the environment of tissue 140. In one example, link 162 is driven by a modulated electrical signal which produces a similarly modulated electric field 151. Further figures include similar features. Capacitance links 162-168 can include wires, shields, coaxial links, twisted pair links, or other electrical links, including combinations thereof.

Capacitance nodes 182-189 comprise elements to induce associated electric field signals 151-155 in the environment of tissue 140 and detect an electric field in the environment of tissue 140. In some examples, each capacitance node comprises a capacitor plate. Capacitance nodes 182-189 can be co-planar, single plate, fringe field or other capacitor styles using at least tissue 140 as a dielectric or as a plate of a capacitor system. Electric field signals 151-155 typically comprise one or more modulated signals which are induced as a variable electrostatic field in the environment and tissue 140. The modulation frequency can be 10 kHz-50 GHz, among others, and include sine wave, square wave, or other signal characteristics. Electric field signals 151-155 can be a modulated signal selected based on the environment around tissue 140, anticipated or detected interference, patient parameters (skin type, size, shape), maximum sensitivity to motion of patient/sensor, or other factors. In some example, the modulation signal of electric field signals 151-155 can be selected to not interfere with the optical drive frequency used in modulation of optical signal 150 or to not interfere with other physiological measurement equipment monitoring the patient. The modulation signal electric field signals 151-155 can be selected to interfere constantly with the optical signal 150 by driving one at a multiple of the other frequency. Alternatively, capacitive measurement using electric field signals 151-155 can be performed when an optical measurement is not being presently performed. In further examples, the modulation signal of electric field signals 151-155 can be swept through a range of modulation frequencies, such as to find an optimal frequency or to reduce dependency of the measurement of electric field signal 151 on various forms of interference. Frequency hopping, chirping, or spread spectrum techniques can also be employed to minimize interference of simultaneous measurement using multiple electric field signals.

In the examples of capacitance nodes, the associated capacitor plates can be positioned on tissue 140, or located proximate and separated by a gap or distance from tissue 140. The gaps between tissue 140 and ones of capacitance nodes can include air, dielectric materials, pads, coatings, adhesives, gels, clothing of the patient, or other dielectric materials.

In further examples, ones of capacitance nodes 182-189 comprise a Faraday shield or electromagnetic interference (EMI) shield associated with link 160 or 161. The shield of link 160 or 161 can be repurposed as a plate of a capacitor and thus driven to create or monitor an electric field signal. Changes in electric field signals can also be detected using the shield. In further examples, optical node 180 or 181 includes a Faraday shield or EMI shield which surrounds associated optical or electrical elements of optical node 180 or 181. This Faraday shield or EMI shield associated with optical node 180 or 181 can be used as a capacitor plate to generate electric field signals and detect changes in electric field signals. The patient under measurement can also be electrically grounded in some single-plate capacitor examples. Further examples of a Faraday shield and other twisted pair arrangements are discussed in FIGS. 16 and 17.

In some examples of capacitance nodes, a single-plate capacitor is employed and positioned on one side of tissue 140. The return path or ground connection of a single-plate single-side capacitor configuration is typically tissue 140 and the earth or nearby structural environment around tissue 140. In other examples, capacitance nodes comprise two plate elements positioned next to each other but on the same side of tissue 140. In two-plate, single-side configurations, plates of capacitance nodes can be positioned on the same side of the fingertip as each other. One plate of a capacitance node can be the 'positive' or driven portion, while the other plate of a capacitance node can be the 'negative' or return/ground/reference portion. Other configurations of signal polarity can be employed. In yet other examples, such as FIGS. 5-6, a two separate single-plate capacitors which are positioned on a different sides of tissue 140 are employed. A first measurement can be performed using a two-plate, two-side measurement with a first plate of a capacitance node and a second plate of another capacitance node. A second measurement can be performed using a single-plate, single-side measurement with the first plate of a capacitance node. A third measurement can be performed using a single-plate, single-side measurement with the second plate of another capacitance node.

In further examples of capacitance nodes, a capacitive touch surface or touch screen can be employed. A capacitive touch surface or touch screen can detect pressure and touch of tissue on the touch screen and can be used to detect sensor on/off conditions, among assisting with optical measurement of physiological parameters.

Links 170-171 each use metal, glass, optical, air, space, or some other material as the transport media, and comprise analog, digital, RF, optical, modulated, or power signals, including combinations thereof. Links 170-171 can each use various communication protocols or formats, such as Serial Peripheral Interface (SPI), Synchronous or Asynchronous Serial Ports, external bus interface, Controller Area Network (CAN) bus, Inter-Integrated Circuit (I2C), 1-Wire, Radio Frequency Identification (RFID), optical, circuit-switched, Internet Protocol (IP), Ethernet, wireless, Bluetooth, communication signaling, or some other communication format, including combinations, improvements, or variations thereof. Links 170-171 can each be direct links or may include intermediate networks, systems, or devices, and can each include a logical network link transported over multiple physical links.

Links 160-168 and 170-171 may each include many different signals sharing the same associated link, as represented by the associated lines in FIGS. 1, 3, 5, and 7, comprising channels, forward links, reverse links, user communications, overhead communications, frequencies, wavelengths, carriers, timeslots, spreading codes, logical transportation links, packets, or communication directions.

The measurement systems discussed above in FIGS. 1-8 can be applied to further examples. Some of the examples are discussed below in FIGS. 9-19, although it should be understood that different measurement systems and associated elements can be employed in FIGS. 9-19.

Figure 9:
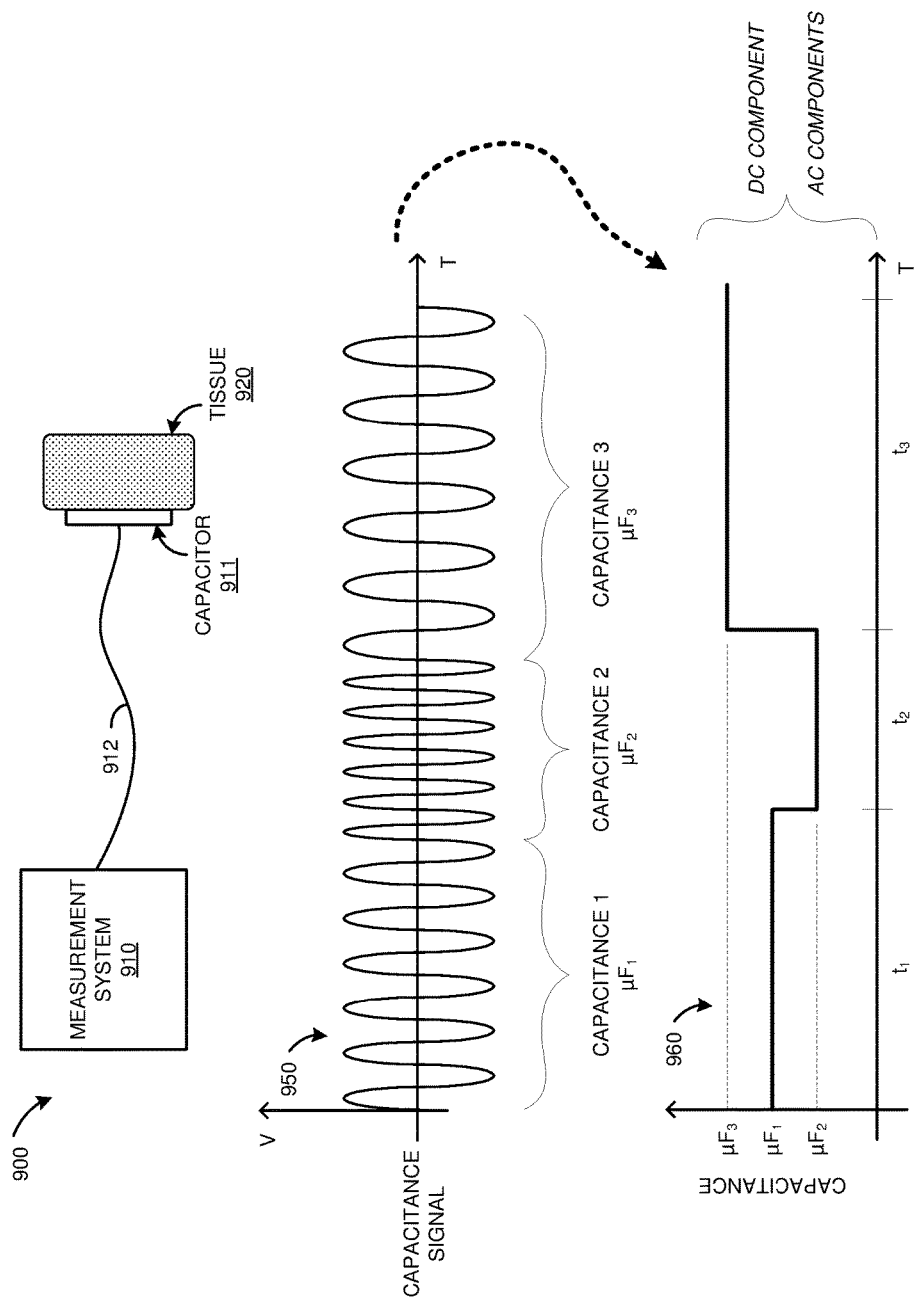
FIG. 9 is a diagram illustrating measurement of physiological parameters.

FIG. 9 is a diagram illustrating measurement of physiological parameters. FIG. 9 includes measurement environment 900, graph 950, and graph 960. Measurement environment 900 includes measurement system 910, capacitor 911, and measurement link 912, with capacitor 911 configured to measured properties of tissue 920. In operation, measurement system 910 drives a modulated electrical signal onto link 912 to drive capacitor 911 and measure tissue 920. In this example capacitor 911 is a single-side, single-plate capacitor, although it should be understood that a two-plate capacitor or a multi-side, single-plate capacitor can instead be employed.

Graph 950 illustrates an example capacitance signal as found on link 912. The capacitance signal can be representative of a changing capacitance as monitored by measurement system 910, such as due to changes in an electric field signal applied to tissue 920. In one example, capacitor 911 can be included in an oscillator circuit along with circuit elements of measurement system 910 to establish a modulated electric field signal in tissue 920. The capacitance measured for capacitor 911 by measurement system 910 can vary in time due to a corresponding change in the dielectric environment of capacitor 911. The dielectric environment of capacitor 911 can change due to changes in many factors, such as tissue 920, the environment of tissue 920, motion of tissue 920, and variation in internal elements of tissue 920, among others. These capacitance changes can be seen in graph 950 as a change in oscillation frequency of the capacitance signal. Graph 950 is simplified to emphasize changes in frequency or wavelength of the measurement signal. In other examples, noise, amplitude variations, rapid frequency changes, and other signal variations can be observed. To identify graph 950, a capacitance monitoring circuit or system can be employed, such as a capacitance to digital converter circuit. In other examples, a power or current draw of a circuit that includes capacitor 911 is monitored to determine the change in capacitance and graph 950. Other techniques can be employed, such as monitoring transmission line capacitive coupling.

Graph 960 illustrates the changes in capacitance over time as detected by measurement system 910. Graph 960 can be derived from graph 950 by determining changes in capacitance based on the frequency changes in graph 950. Link 912 indicates a first capacitance for time $t_1$, a second capacitance for time $t_2$, and a third capacitance for time $t_3$. Although the changes in capacitance in this example are highly simplified, real-world measurements can include changes in noise, dynamic AC components, DC shifts, among other factors. These various changes in capacitance can be used to extract characteristics of the capacitance signal to determine physiological parameters, such as hemoglobin measurements, and also to aid in physiological measurements made with optical sensing equipment, such as PPG measurements. Further examples of capacitance enhanced measurements are discussed below.

The various signal components of the measured capacitance signal can include components that are representative of physiological parameters, or can be used to calculate physiological parameters, such as hemoglobin parameters. For example, AC components and DC components of the capacitance signal can be compared or correlated to determine hemoglobin parameters or changes in hemoglobin parameters of a patient. In further examples, AC components and DC components of the capacitance signal can be processed to determine breathing rates, pulse rates, ECG information, and other physiological parameters discussed herein.

In further examples, one or more portions of system 900 can be incorporated into a wearable device. For example, at least capacitor 911 can be incorporated into a fitness wristband for monitoring of physiological parameters during fitness activities. This fitness wristband can include moisture and sweat protection to isolate elements of system 900 from environmental exposure. Capacitance measurements for fitness can include breathing rate, heart rate, sweat levels, electrolyte loss rate, running pace, and changes thereto. In some examples, all elements of system 900 are included in the fitness wristband, with capacitor 911 configured to be located next to tissue of the fitness participant when the wristband is worn.

Figure 10:
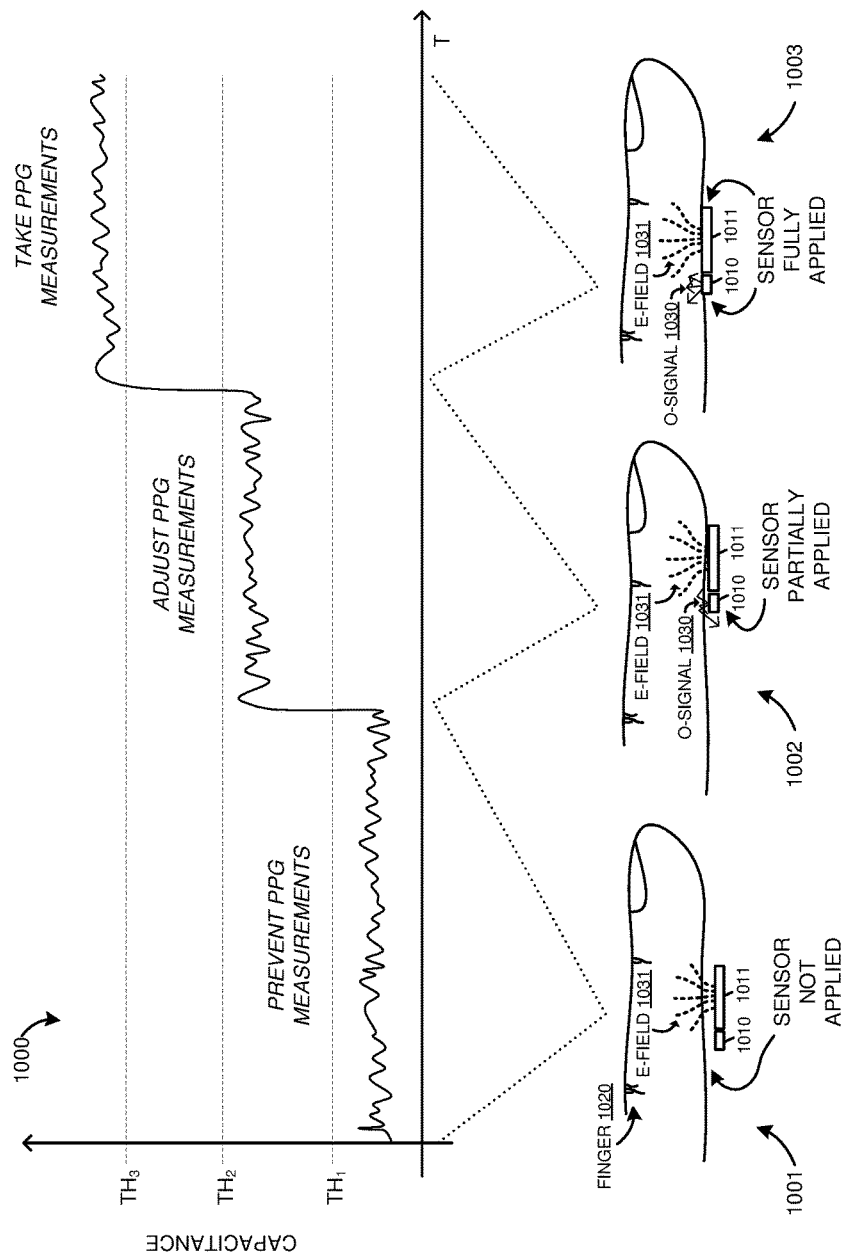
FIG. 10 is a diagram illustrating measurement of physiological parameters.

FIG. 10 is a diagram illustrating measurement of physiological parameters. FIG. 10 includes graph 1000 and associated pressure configurations 1001-1003. FIG. 10 illustrates capacitance-based identification of pressure changes that may affect PPG measurements, although the identification of pressure changes can be applied to other physiological measurements. FIG. 10 includes three different sensor configurations, namely a "sensor not applied" configuration 1001, a "sensor partially applied" configuration 1002, and a "sensor fully applied" configuration 1003. Each pressure configuration 1001-1003 corresponds to a different region on graph 1000, as indicated by the dotted lines. Graph 1000 includes an x-axis which represents "time" (T) and a y-axis which represents "capacitance" which can be measured in Farads, such as picofarads (pF). Three capacitance thresholds are indicated in graph 1000, namely threshold 1 ($TH_1$), threshold 2 ($TH_2$), and threshold 3 ($TH_3$), and will be discussed in greater detail below.

Each configuration 1001-1003 includes optical sensor 1010 and capacitance sensor 1011 as applied to finger 1020. Optical sensor 1010 is configured to emit and detect optical signal 1030 in finger 1020 to determine a PPG waveform. Capacitance sensor 1011 is configured to emit and detect electric field signal 1031 in proximity to finger 1020. Optical sensor 1010 can include elements discussed herein for optical nodes 180-181 in FIGS. 1-8, although variations are possible. Capacitance sensor 1011 can include elements as discussed herein for capacitance nodes 182-189 in FIGS. 1-8, although variations are possible. In this example, capacitance sensor 1011 comprises a single plate capacitor, and uses at least finger 1020 as a dielectric for the single plate capacitor. In further examples, two-plate capacitors can be employed.

Optical sensor 1010 and capacitance sensor 1011 can be coupled together physically, and share a common structural support. The common structural element can allow for contact of sensor elements with finger 1020. This common structural support can comprise a rigid carrier, such as clip-on finger probe, or can include a flexible carrier such as an adhesive pad that can be fit onto finger 1020. Further examples of pads are discussed in FIGS. 15 and 16.

Although omitted for clarity in FIG. 10, optical sensor 1010 can be coupled to further measurement equipment and systems, such as processing system 110 or optical system 121 in FIGS. 1-8, although variations are possible. Also, although omitted for clarity in FIG. 10, capacitance sensor 1011 can be coupled to further measurement equipment and systems, such as processing system 110 or capacitance system 130 in FIGS. 1-8, although variations are possible.

Finger 1020 is shown as representing tissue under measurement by sensors 1010-1011. Other tissue portions can instead be included, such as a forehead, chest, toe, limb, or other tissue of a patient, including combinations thereof.

A capacitance level measured by capacitance sensor 1011 can relate to a pressure of capacitance sensor 1011 on finger 1020. FIG. 10 indicates three discrete pressure configurations of the sensors onto finger 1020 as correlated to three different capacitance thresholds, $TH_1$, $TH_2$, and $TH_3$. Although various random noise might be detected by capacitance sensor 1011, a DC component can be correlated to a pressure of capacitance sensor 1011 on finger 1020 and a pressure of likewise optical sensor 1010 on finger 1020. Also, motion noise based at least on movement of finger 1020 or elements internal to finger 1020 can be measured by capacitance sensor 1011. However, this motion noise typically leads to AC components of the capacitance signal measured by capacitance sensor 1011. Further examples of motion detection are discussed in at least FIG. 11A below.

Configuration 1001 shows a "sensor not applied" condition. In configuration 1001, capacitance sensor 1011 measures a first capacitance level, as indicated in graph 1000. This first capacitance level might have a certain amount of random noise in it, but on average, the first capacitance level is below a first capacitance threshold ($TH_1$). When the average capacitance level measured by capacitance sensor 1011 is below $TH_1$, then an associated measurement system can determine that optical sensor 1010 has not been properly applied to finger 1020. The capacitance level can be affected by finger 1020 due to finger 1020 being too far away from the capacitor portion of capacitance sensor 1011 or the sensor portions completely off finger 1020, thus providing a first level of dielectric influence for the capacitor portion of capacitance sensor 1011.

When the capacitance level is below $TH_1$, then the measurement system associated with optical sensor 1010 can at least prevent optical signal 1031 from being emitted. The measurement system can turn off optical emitter elements of optical sensor 1010, such as removing power from a laser diode or LED portion of optical sensor 1010 that emits optical signal 1031. By turning off the power to the emitter portion of optical sensor 1010, the measurement system can save power and allow associated equipment to operate in a low power mode, or a battery-save mode. Additionally, the measurement system can prevent measurement and determination of physiological parameters when optical sensor 1010 is not properly applied to finger 1020, preventing erroneous or inaccurate measurement results when optical sensor 1010 is not properly applied. Furthermore, various alarms for healthcare professionals or measurement systems that are related to physiological measurement of finger 1020 can be modified or disabled due to optical sensor 1010 not properly on finger 1020. Configuration 1001 can prompt an associated measurement system to alert or signal an operator of the measurement system than the sensor has not been applied properly. Configuration 1001 can prompt an associated measurement system to alert or signal that any associated optical measurements taken are potentially inaccurate.

Configuration 1002 shows a "sensor partially applied" condition. In configuration 1002, capacitance sensor 1011 measures a second capacitance level, as indicated in graph 1000. This second capacitance level might have a certain amount of random noise in it, but on average, the second capacitance level is below a second capacitance threshold ($TH_2$) and above the first capacitance level ($TH_1$). When the average capacitance level measured by capacitance sensor 1011 is below $TH_2$, but above $TH_1$, then an associated measurement system can determine that optical sensor 1010 has been only partially applied to finger 1020. The capacitance level can be affected by finger 1020 due to finger 1020 being too far away from the capacitor portion of capacitance sensor 1011, not having enough pressure applied by the sensor portions onto finger 1020, or the surface area of the sensor portions not contacting finger 1020 a desired amount, and thus providing a second level of dielectric influence for the capacitor portion of capacitance sensor 1011.

When the capacitance level is below $TH_2$, but above $TH_1$, then the measurement system associated with optical sensor 1010 can adjust measurement of physiological parameters, and can act in a few different ways. In a first example, the measurement system can at least prevent optical signal 1031 from being emitted, prevent optical measurement from occurring, or prevent an alarm from being produced, much like when the average capacitance level is below $TH_1$. In a second example, the measurement system can instead perform optical measurement using optical sensor 1010 but modify the measurement based on the capacitance level. For example, the measurement system can identify an average capacitance level of a capacitor of capacitance sensor 1011 and scale optical measurement by optical sensor 1010 based on at least the capacitance level. The scaling can encompass selecting calculation coefficients for calculating physiological parameters based on optical signal 1031, such as calculations used in determining a PPG. The scaling can encompass changing an amplification level associated with signal processing elements used in optical detection and optical measurement using optical signal 1031. In a third example, an intensity level of optical signal 1031 can be modified based on the capacitance level, so that at a lower capacitance level a higher intensity of optical signal 1031 is employed and at a higher capacitance level a lower intensity is employed for optical signal 1031. As with configuration 1001, configuration 1002 can prompt an associated measurement system to alert or signal an operator of the measurement system than the sensor has not been applied properly. Configuration 1002 can prompt an associated measurement system to alert or signal that any associated optical measurements taken are potentially inaccurate.

Configuration 1003 shows a "sensor fully applied" condition. In configuration 1003, capacitance sensor 1011 measures a third capacitance level, as indicated in graph 1000. This third capacitance level might have a certain amount of random noise in it, but on average, the third capacitance level is above a third capacitance threshold ($TH_3$). When the average capacitance level measured by capacitance sensor 1011 is above $TH_3$, then an associated measurement system can determine that optical sensor 1010 has been fully or properly applied to finger 1020. The capacitance level above $TH_3$ can occur when the sensors are applied at a desired pressure and contact area to finger 1020, and thus providing a third level of dielectric influence for the capacitor portion of capacitance sensor 1011.

When the capacitance level is above $TH_3$, then the measurement system associated with optical sensor 1010 can emit optical signal 1031 into finger 1020. The measurement system can turn on optical emitter elements of optical sensor 1010, such as providing power to a laser diode or LED portion of optical sensor 1010 that emits optical signal 1031. By turning on the power to the emitter portion of optical sensor 1010 only above $TH_3$, the measurement system can save power and allow associated equipment to operate in a low power mode until sensor portions are properly applied to finger 1020. Additionally, the measurement system can now measure and determine physiological parameters, such PPG measurement, when optical sensor 1010 is properly applied to finger 1020, preventing erroneous or inaccurate measurement results when optical sensor 1010 is not properly applied. Configuration 1003 can prompt an associated measurement system to alert or signal an operator of the measurement system than the sensor has been applied properly. Configuration 1003 can prompt an associated measurement system to alert or signal that any associated optical measurements taken are accurate.

In further examples, the measurement system can process the properties of one or more electric field signals to determine a where on the body of a patient a capacitor plate has been placed or located. This determination can help to identify an improper location of the plate on the patient. In some examples, a user interface included in the measurement system is configured to alert an operator of the measurement system when the placement comprises the at least one capacitor plate improperly applied to the tissue of the patient. For example, different locations on the body, such as a finger, ear, nose, forehead, or other location, exhibit different electric field properties, capacitance, change in capacitance, or capacitance measurements. These differences may be measured and noted, such as by measuring them at different modulation frequencies, to first characterize various body locations. Later, when sensor portions are placed on tissue, the capacitance system can measure these properties to identify where the sensor has been placed. For example, the system can determine that the sensor has been placed on a forehead instead of a finger. Measurement parameters can be modified based on the body location and placement, such as loading correct calculation coefficients based on the placement or body location. An error message or alert can be provided to an operator if a sensor that is designed for one or more body locations is applied to a different or incompatible body location.

In addition to placement of a sensor on a particular body part of a patient, properties of the tissue can be detected. For example, a skin type, skin moisture content, skin elasticity, or other tissue parameters can be identified with a capacitance signal. Measurements of physiological signals, such as optical measurements, can be corrected or adjusted based on the skin or tissue parameters identified by the capacitance signal, such as scaling calculation coefficients, adjusting intensity of measurement signal sources, adjusting sensitivity or gain of detection elements, among other adjustments, including combinations thereof.

Figure 11A:
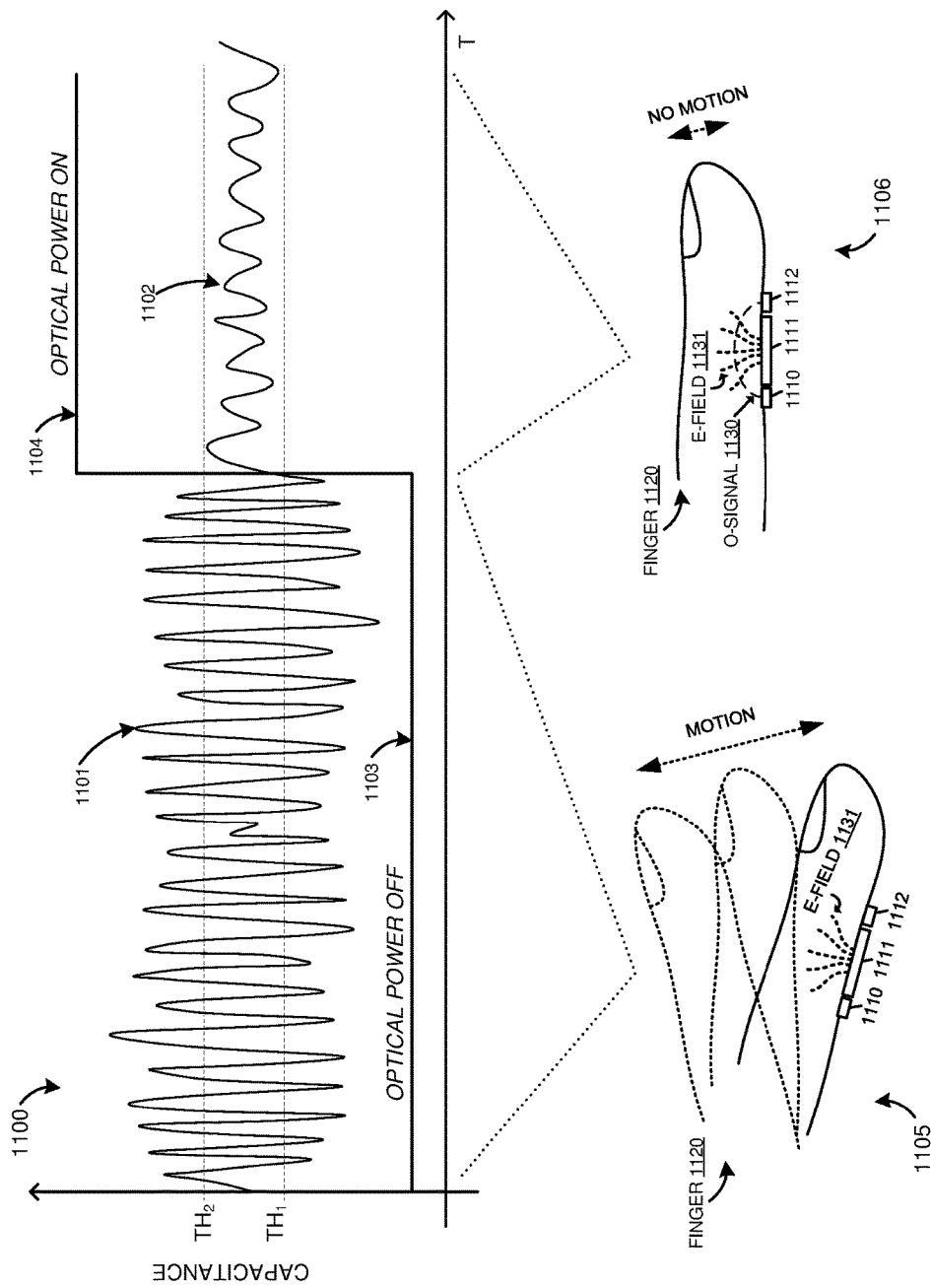
FIG. 11A is a diagram illustrating measurement of physiological parameters.
Figure 11B:
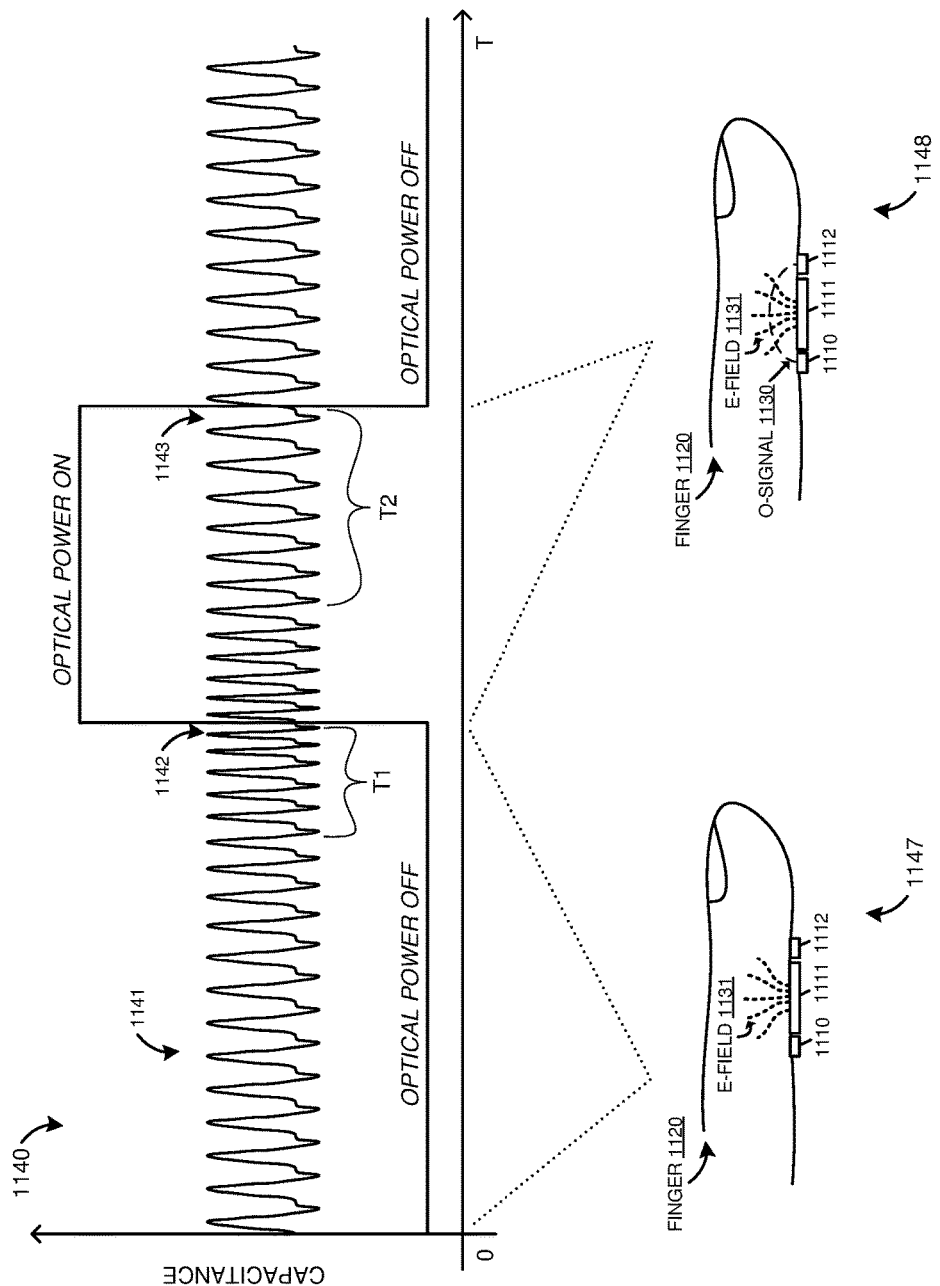
FIG. 11B is a diagram illustrating measurement of physiological parameters.

FIG. 10, discussed above, changes in average or "DC" capacitance levels due to pressure of a capacitance sensor on tissue. FIGS. 11A-11B, in contrast, discusses dynamic changes or "AC" capacitance levels due to dynamic conditions, such as movement or motion of tissue undergoing measurement (FIG. 11A) or due to changing physiological characteristics of the tissue or patient undergoing measurement (FIG. 11B), among other dynamic conditions, including combinations thereof.

FIG. 11A is a diagram illustrating measurement of physiological parameters. FIG. 11A includes graph 1100 and two different motion configurations, namely a "sensor in motion" configuration 1105, and a "sensor not in motion" configuration 1106. Each motion configuration 1105-1106 corresponds to a different region on graph 1100, as indicated by the dotted lines. Graph 1100 includes an x-axis which represents "time" (T) and a y-axis which represents "capacitance" which can be measured in Farads, such as picofarads (pF). A capacitance threshold region is indicated in graph

1100, namely the region between threshold 1 (TH$_1$) and threshold 2 (TH$_2$), and will be discussed in greater detail below.

Each sensor configuration 1105-1106 includes optical emitter 1110, optical detector 1112, and capacitance node 1111 as applied to finger 1120 or other patient tissue. Optical emitter 1110 is configured to emit optical signal 1130 in finger 1120. Optical detector 1112 is configured to detect optical signal 1130 after propagation in finger 1120. Capacitance node 1111 is configured to emit and detect electric field signal 1131 in proximity to finger 1120. Optical emitter 1110 and optical detector 1112 can include elements discussed herein for optical nodes 180-181 in FIGS. 1-8, although variations are possible. Capacitance node 1111 can include elements as discussed herein for capacitance nodes 182-189 in FIGS. 1-8, although variations are possible. In this example, capacitance node 1111 comprises a single plate capacitor, and uses at least finger 1120 as a dielectric for the single plate capacitor. In further examples, two-plate capacitors can be employed.

Optical emitter 1110, optical detector 1112, and capacitance node 1111 can be coupled together physically, and share a common structural support. The common structural element can allow for contact of sensor elements with finger 1120. This common structural support can comprise a rigid carrier, such as clip-on finger probe, or can include a flexible carrier such as an adhesive pad that can be fit onto finger 1120. Further examples of pads are discussed in FIGS. 15-17.

Although omitted for clarity in FIG. 11A, optical emitter 1110 and optical detector 1112 can be coupled to further measurement equipment and systems, such as processing system 110 or optical system 121 in FIGS. 1-8, although variations are possible. Also, although omitted for clarity in FIG. 11A, capacitance node 1111 can be coupled to further measurement equipment and systems, such as processing system 110 or capacitance system 130 in FIGS. 1-8, although variations are possible. Finger 1120 is shown as representing tissue under measurement by sensors 1110-1112. Other tissue portions can instead be included, such as a forehead, chest, toe, limb, or other tissue of a patient, including combinations thereof.

Configuration 1105 shows a "sensor in motion" condition. In configuration 1105, capacitance node 1111 measures a capacitance signal 1101, as indicated in graph 1100. This capacitance signal might include large variations, such as AC noise due to motion of finger 1120 or motion of components within finger 1120. These large variations can be considered to be a noise component of the capacitance signal. The variation can be periodic and correlated to a movement of finger 1120, such as when finger 1120 is being "waved" regularly or tapped against a surface. The variation can be quasi-random, such as when finger 1120 is being moved in a random manner. Motion of components within finger 1120 can also contribute to an AC noise signal, such as due to sloshing of blood in vessels of finger 1120. Each peak or valley in signal 1101 of graph 1100 might correspond to an impulse of movement experienced by finger 1120, such as sudden change in direction or motion. Motion artifacts can also be related to changes in sensor contact pressure with body tissue. The capacitive sensor of FIG. 11A also detects movements of the sensor relative to finger 1120, such as due to changes in sensor contact pressure.

As shown in graph 1100, capacitance signal 1101 has a variation level that exceeds a noise threshold range (TH$_1$-TH$_2$). That is, the amplitude of the AC portion of signal capacitance 1101 is larger than a threshold, such as the difference between two capacitance levels TH$_1$ and TH$_2$. As with FIG. 9, the capacitance level can be affected by finger 1120 due to finger 1120 being too far away from the capacitor portion of capacitance node 1111, a sensor misapplication, or sensor contact pressure variation. It should be understood that operations in FIG. 9 can be combined with operations in FIG. 11A.

When the capacitance level measured by capacitance node 1111 rises above and falls below the threshold range TH$_1$-TH$_2$, or when the AC amplitude of capacitance signal 1101 exceeds a threshold amount, then an associated measurement system can determine that too much noise due to motion will also occur for any optical measurement performed by optical detector 1112. Accordingly, the associated measurement system can disable measurement of optical signals in finger 1120 when the capacitance level exceeds the threshold range. Optical emitter 1110 can have power turned off when the capacitance level or noise exceeds the threshold range, such as indicated by "optical power off" signal 1103 in graph 1100. The measurement system removes power from a laser diode or LED portion of optical emitter 1110 that emits optical signal 1130. By turning off the power to optical emitter 1120, the measurement system can save power and allow associated equipment to operate in a low power mode. Additionally, the measurement system can prevent measurement and determination of physiological parameters when the threshold range is exceeded, preventing erroneous or inaccurate measurement results when motion of finger 1120 can introduce undesirable noise or artifacts into measurement. Alternatively, when the threshold range is exceeded, an associated measurement system can alert or signal an operator of the measurement system than the sensor is experiencing noise or being moved too rapidly. An associated measurement system can alert or signal an operator that any associated optical measurements taken are potentially inaccurate. Although a threshold capacitance range is discussed, in other examples a magnitude of noise in signal 1101 or an amplitude of signal 1101 might exceed a threshold level.

When the capacitance level measured by capacitance node 1111 falls within the threshold range, then an associated measurement system can enable measurement of optical signals in finger 1120. Signal 1102 of graph 1100 can indicate a low motion or low noise condition. Optical emitter 1110 can have power turned on when the capacitance level or noise falls within the threshold range, such as indicated by "optical power on" signal 1104 in graph 1100. The measurement system supplies power to a laser diode or LED portion of optical emitter 1110 that emits optical signal 1130.

The measurement system can perform measurement and determination of physiological parameters when the capacitance signal is within the threshold range, preventing erroneous or inaccurate measurement results when motion of finger 1120 can introduce undesirable noise or artifacts into measurement. An associated measurement system can alert or signal an operator that any associated optical measurements taken are accurate regarding motion-based noise. For example, when an optical measurement is experiencing a noisy condition, such as due to motion-based noise or other noise sources, a display on the measurement system can indicate to an operator that the optical measurement is currently noisy or exceeds a noise threshold for accurate measurement. In further examples, a capacitance signal, such as measured by capacitance node 1111, can be used as a trigger for displaying physiological parameters on a monitor or display when a threshold condition is met.

When the capacitance level measured by capacitance node 1111 rises above and falls below the threshold range $TH_1$-$TH_2$, or when the AC amplitude of capacitance signal 1101 exceeds a threshold amount, then an associated measurement system can detect that the tissue under measurement is in motion. This capacitance-based motion detection can be employed to monitor movement of a patient, such as movement of a baby in a NICU environment, or to monitor movement of a comatose or bed-ridden patient. When the capacitance level measured by capacitance node 1111 falls within the threshold range, then an associated measurement system can detect that the tissue under measurement is not in motion. Multiple body parts can be monitored using multiple capacitive motion sensors to determine when various limbs, head, body, or other body parts are moved. Additionally, the patterns of capacitance signals 1101-1102 can be characterized. This characterization can include identifying patterns or 'fingerprints' in the motion-based noise. For example, a finger tapping can be characterized as a first pattern, while a hand waving can be characterized by a second pattern. The patterns can comprise patterns in amplitude, frequency, phase, or other characterizations. Measured patterns can be compared against a database of previously determined patterns to establish the particular movement or motion type. Motion of the patient or the tissue under measurement can be used to alert medical personnel or logged by the measurement system. The alerts or logs can indicate what pattern of motion is occurring or which limb is being moved by the patient.

FIG. 11B is a diagram illustrating measurement of physiological parameters. FIG. 11B includes some similar elements at FIG. 11A, such as elements 1110-1112, 1120, and 1130-1131, although variations are possible. FIG. 11B includes graph 1140 and two different optical sensor power configurations, namely an "optical power off" configuration 1147, and an "optical power on" configuration 1148. Each configuration corresponds to a different region on graph 1140, as indicated by dotted lines below graph 1140. Graph 1100 is a graph of a physiological parameter and includes an x-axis which represents "time" (T) and a y-axis which represents "capacitance" which can be measured in Farads, such as picofarads (pF).

Each configuration 1147-1148 includes optical emitter 1110, optical detector 1112, and capacitance node 1111 as applied to finger 1120 or other patient tissue. Optical emitter 1110 is configured to emit optical signal 1130 in finger 1120. Optical detector 1112 is configured to detect optical signal 1130 after propagation in finger 1120. Capacitance node 1111 is configured to emit and detect electric field signal 1131 in proximity to finger 1120. Optical emitter 1110 and optical detector 1112 can include elements discussed herein for optical nodes 180-181 in FIGS. 1-8, although variations are possible. Capacitance node 1111 can include elements as discussed herein for capacitance nodes 182-189 in FIGS. 1-8, although variations are possible. In this example, capacitance node 1111 comprises a single plate capacitor, and uses at least finger 1120 as a dielectric for the single plate capacitor. In further examples, two-plate capacitors can be employed. Although omitted for clarity in FIG. 11B, optical emitter 1110 and optical detector 1112 can be coupled to further measurement equipment and systems, such as processing system 110 or optical system 121 in FIGS. 1-8, although variations are possible. Also, although omitted for clarity in FIG. 11B, capacitance node 1111 can be coupled to further measurement equipment and systems, such as processing system 110 or capacitance system 130 in FIGS. 1-8, although variations are possible. Finger 1120 is shown as representing tissue under measurement by sensors 1110-1112. Other tissue portions can instead be included, such as a forehead, chest, toe, limb, or other tissue of a patient, including combinations thereof.

Capacitance node 1111 measures a capacitance signal 1141, as indicated in graph 1140. This capacitance signal might include variations due to a physiological parameter, such as a pulse, breathing rate, or heart rate, among others. Noise and motion artifacts can also be included in capacitance signal 1141, such as discussed in FIG. 11A, but these artifacts are omitted in this example for clarity.

Optical power is applied to optical emitter 1110 as-needed to ensure a targeted level of detail in measurement of the physiological parameter monitored by capacitance node 1111. Capacitance node 1111 can monitor the physiological parameter, but the associated capacitance signal might have a lower accuracy or lower resolution than an optical system. Thus, capacitance node 1111 is employed to provide a less accurate measurement of a physiological parameter until a more accurate measurement is desired. In this example, if the patient is in a steady-state or stable condition at a certain time, then the optical power can be in an 'off' condition for optical emitter 1110 to reduce power consumption and reduce any associated data logging requirements. At some point, the physiological parameter that is monitored by capacitance node 1111 crosses a parameter threshold and a higher accuracy reading is desired. Responsive to the physiological parameter crossing the physiological threshold, a measurement system can enable measurement using an optical signal, namely optical signal 1130. Once the physiological parameter has dropped below a physiological threshold, then the optical power can be removed again and optical measurement can be suspended.

In the example shown in FIG. 11B, graph 1140 illustrates a rhythmic capacitance signal that indicates a rhythmic physiological parameter, such as a pulse rate, heart rate, breathing rate, and the like. The rhythm of physiological parameter can vary in frequency over time, such as due to health or stability changes in the patient being monitored. Notably, during time T1 the capacitance signal increases in frequency and during time T2 the capacitance signal decreases in frequency. A rising frequency threshold is reached at point 1142 which triggers optical measurement using optical signal 1130. This optical measurement continues for the physiological parameter until another falling frequency threshold is reached at point 1143 which halts optical measurement using optical signal 1130. Steady-state measurement using the capacitance signal can continue after the optical measurement has ceased.

It should be noted that the measurement or non-measurement using optical signal 1130 can be achieved in several ways. In a first example, such as shown in graph 1140, power to optical emitter 1110 or optical detector 1112 can be selectively provided or removed to enable or disable the associated optical measurement elements. An associated measurement system can supply or remove power to a laser diode or LED portion of optical emitter 1110 that emits optical signal 1130. In a second example, power can remain active for optical emitter 1110 or optical detector 1112, but a measurement system can ignore measurements using the optical systems when not desired.

Multiple body parts can be monitored using multiple capacitive motion sensors to determine when more accurate measurement of physiological parameters for various limbs, head, body, or other body parts are desired. In some examples, the patterns of capacitance signal 1141 can be characterized. This characterization can include identifying patterns or 'fingerprints' in the physiological parameters monitored by capacitance node 1111. The patterns can comprise patterns in amplitude, frequency, phase, or other characterizations that trigger a measurement signal to monitor the physiological parameter optically, or using other measurement apparatuses. Measured patterns can be compared against a database of previously determined patterns to establish the particular threshold or pattern. Enabling or disabling of the optical measurement can also alert medical personnel to a change in patient condition or can be logged by the measurement system.

Figure 12:
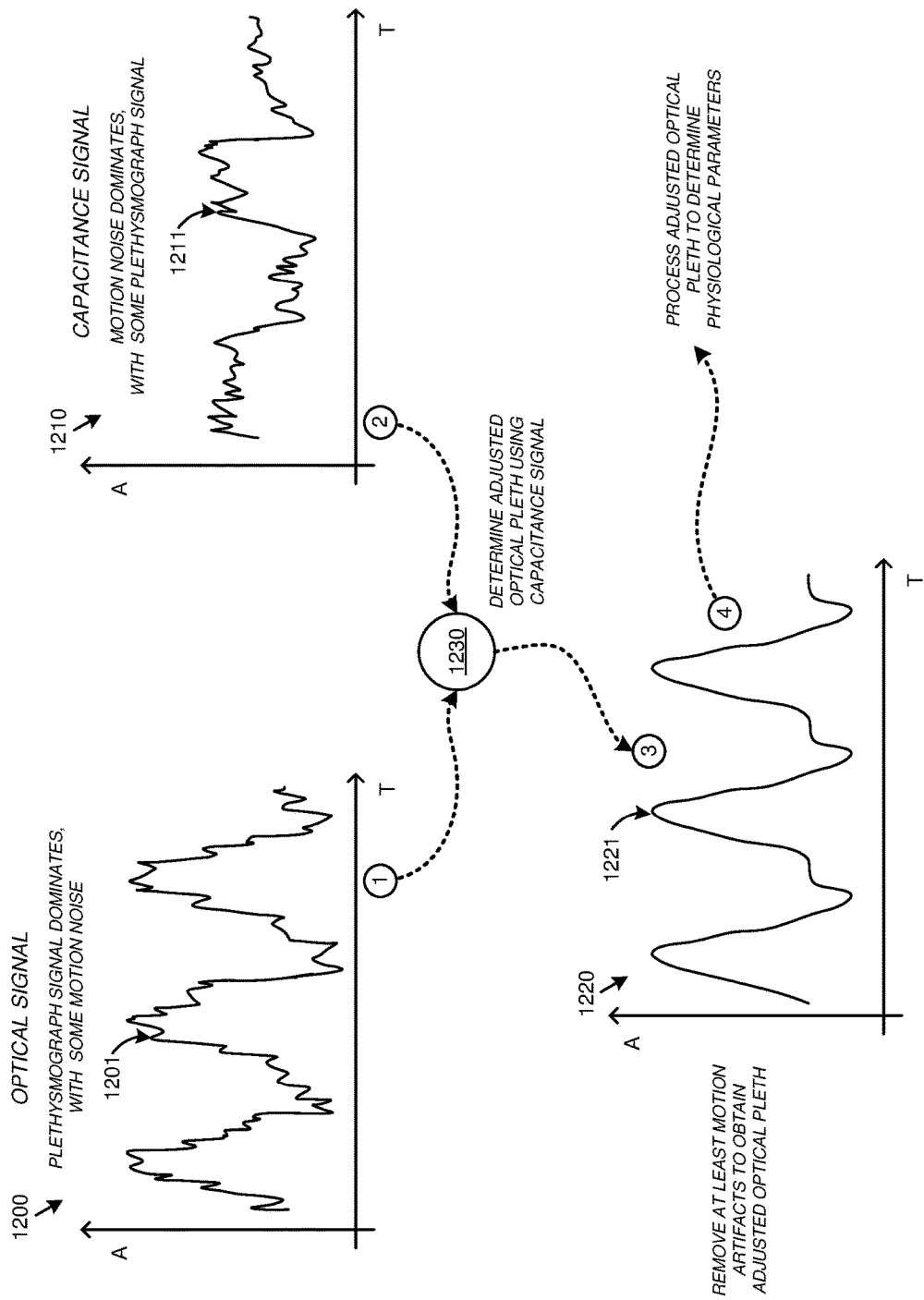
FIG. 12 is a diagram illustrating measurement of physiological parameters.

FIG. 12 is a diagram illustrating measurement of physiological parameters. FIG. 12 includes three graphs, namely optical signal graph 1200, capacitance signal graph 1210, and processed graph 1220. FIG. 12 illustrates one example process to identify a corrected plethysmograph of tissue of a patient. Data from optical and capacitance measurements are processed to identify a plethysmograph with motion and noise artifacts removed. The processing of the various data can be performed by any measurement system or processing system discussed herein, such as processing system 110 of FIGS. 1-8. Processing node 1230 is also included to illustrate an example processing system that processes the various signals in FIG. 12 to identify a corrected plethysmograph. Processing node 1230 can include elements of any processing system as discussed herein.

Graph 1200 illustrates optical signal 1201 formed from data derived from an optical measurement of tissue. In typical examples, graph 1200 represents a PPG which comprises an optically measured plethysmograph, such as performed using optical system 121 of FIG. 1B. However, optical signal 1201 includes various noise elements, such as due to motion or other noise sources. In graph 1200, the plethysmograph signal dominates, with motion noise layered on top of the plethysmograph signal.

Graph 1210 illustrates capacitance signal 1211 formed from data derived from a capacitance-based measurement of tissue. In typical examples, graph 1210 represents a timewise changing capacitance signal, such as performed using capacitance system 130 of FIGS. 1-8 based on changes in electric field signals or capacitance. However, capacitance signal 1211 includes various noise elements, such as due to motion or other noise sources, as well as signal elements of a plethysmograph signal. In graph 1210, the noise artifacts dominate, with a plethysmograph signal layered on top of the motion noise signal. It should be understood that different variations of noise and plethysmograph signals can be measured than those shown in FIG. 12.

Graph 1220 illustrates a processed signal, taking into account signal elements of optical signal 1201 and capacitance signal 1211. A processing system can adjust the optical plethysmograph using the capacitance signal to reduce a noise level in the optical plethysmograph. A processing system can correct the optical plethysmograph using the capacitance signal to reduce a noise level in the optical plethysmograph. In some examples, optical signal 1201 and capacitance signal 1211 are processed to determine common noise elements, such as motion artifacts, due to motion of the tissue under measurement. Common noise elements that are correlated between both signals can be removed from the optical plethysmograph signal by subtracting the capacitance signal, or a scaled or filtered version or portion of the capacitance signal, from signal 1201 to form a smooth PPG signal 1221. This noise cancellation or noise rejection for optical signals can allow for determination of an adjusted PPG 1220. This adjusted PPG can be used to determine physiological parameters to provide enhanced detection of deltaPOP, respiratory rate, respiratory effort, $SpO_2$, heart rate, or other physiological parameters.

Processing node 1230 can be configured to process changes in the one or more electric field signals to determine at least one noise component in the changes in the one or more electric field signals caused by the motion of the tissue of the patient. Processing node 1230 can process the at least one noise component in the changes in the one or more electric field signals to reduce at least one noise component in the one or more optical signals to determine corrected physiological parameters of the patient, such as a corrected plethysmograph. Processing node 1230 can find correlated noise components to select components of the electric field signals to reduce noise in the optical signals. These noise components can be correlated in time, such as correlating transient events due to movement, or can be correlated in frequency, such as correlating certain noise frequencies of the capacitance signal to similar noise frequencies in the optical signal to cancel the noise frequencies out of the optical signal. Wavelet or frequency domain processing can be employed to identify common noise elements between the optical signals and the capacitance signals. These correlated, noisy portions of the capacitive signal can be used to identify and remove noise from the optical signal, such as by subtracting noise components from the optical signal, as discussed herein.

Instead of or in addition to removing noise from the optical signal, processing node 1230 can assign a weighting or quality indicator of the optical signals when the capacitance signals indicated large transient noise events. For examples, processing node 121 can process the one or more optical signals with a first, lower, processing weight when the noise level of the capacitance signal exceeds a noise threshold and process the one or more optical signals with a second, higher, processing weight when the noise level of the capacitance signal does not exceed the noise threshold. Processing node 1230 can identify noisy periods using the capacitance signal and avoid optical measurements during noisy periods, or indicate poor quality of measurements by changing a light or indicator based on a confidence level of the optical measurements. In other examples, where physiological parameters are being logged, a confidence indication can accompany any optical measurements to indicate noisy periods so a user or processing system can give appropriate weighting to optical measurement data.

The capacitance signal can be compared to the optical signal to determine physiological events. These events can include sudden changes or movements of the patient which can indicate a seizure or other transient movement event. Another event includes blood loss by the patient, which can be identified when a capacitance signal remains roughly unchanged but an optical signal deviates greatly, which may occur if a patient is bleeding profusely.

Further signal processing can be performed utilizing both the capacitance based measurements and the optical based measurements. For example, processing node 1230 can determine severity of motion artifacts in a PPG or power of artifacts at certain frequencies of a PPG to determine at what frequencies of a PPG waveform might be corrupt or poor quality. Processing node 1230 can determine impulse response from the capacitance signal and apply this impulse response to a PPG waveform. The impulse response can be employed in a finite impulse response (FIR) filter, where the capacitance signal is input to the FIR, and the FIR output is subtracted from a PPG. Filter coefficients can be adapted over time based on measurements of the capacitance signals.

A fundamental frequency of a PPG can be determined by processing system 1230, and a spectrum of a noise signal can be derived from capacitance signal with a high pass or bandpass filter. The PPG waveform can be filtered to remove noise that is at one or more fundamental frequencies of the noise waveform. In some examples, the fundamental frequencies of the PPG waveform correlate to a heart rate, and noise can be removed from other frequencies to smooth out a signal that contains the remaining fundamental frequencies. A comb filter can be employed by processing system 1230 to extract only heart rate harmonics of a heart rate from a PPG, and eliminate an Nth harmonic of the heart rate signal if the Nth harmonic is found to be excessively noisy as determined by the capacitance signal. The time epoch to calculate the spectrum of noise from the capacitance signal may vary in duration depending on what frequency of noise is to be eliminated. Other methods such as correlations, independent component analysis (ICA), pleth morphology, FFT, or wavelet analysis may be used for noise mitigation or subtraction. Correction of measurements for DC shifts can also be improved by comparing the capacitance signal to a measured physiological signal.

Furthermore, processing node 1230 can process the capacitance signal to provide an input to an ensemble averaging algorithm. This input, which may be referred to as a lock signal, can be employed in ensemble averaging as a clock signal to lock a PPG signal to the clock to improve the ensemble averaging and establish a consistent periodic averaging. In ensemble averaging, the capacitance signal can also be employed to indicate a confidence level for each individual averaging of the ensemble based on a measured noise level. The capacitance signal can be used to determine an instantaneous noise level which can indicate a confidence level of the optical measurement. When the optical measurements are used in an ensemble averaging process, when a high instantaneous noise is monitored for a portion of the optical signal, then that portion of the optical signal can receive a lower weighting in the ensemble average. Less noisy portions of the optical signal can be given a higher weighting in the ensemble average. The weighting can be correlated to a noise level measured by the capacitance signal. In another example, an ensemble average weight can be modified based on likelihood of noise in a physiological parameter, such a PPG. The likelihood of noise can be established by monitoring a capacitance signal and identifying when noise of the capacitance signal indicates a concurrently measured physiological parameter is subject to similar noise. For example, an optical signal used to measure a PPG can have an ensemble average weight modified when a concurrent capacitance measurement indicates noise.

Figure 13:
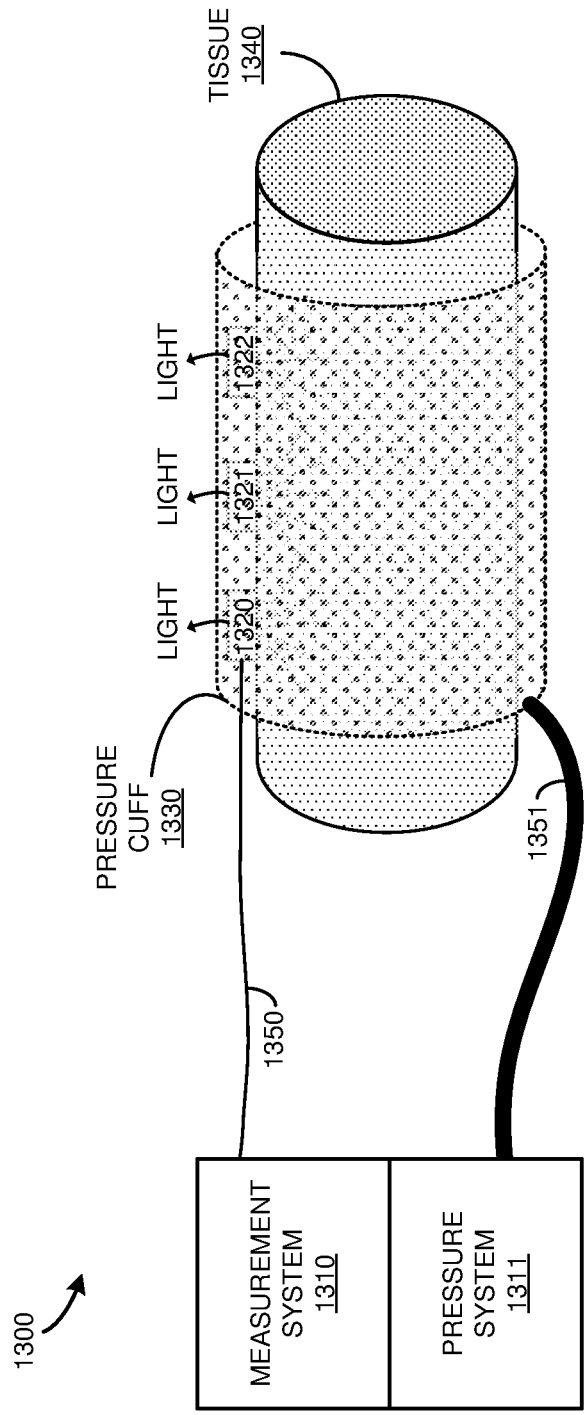
FIG. 13 is a system diagram illustrating a physiological measurement system.

FIG. 13 is a system diagram illustrating physiological measurement system 1300. System 1300 includes measurement system 1310 and pressure system 1311, with capacitive sensors 1320-1322, and pressure cuff 1330 applied to tissue 1340. Measurement system 1310 and capacitive sensors 1320-1322 communicate over link 1350, which can include one or more links for each capacitive sensor.

Pressure system 1311 supplies air pressure to pressure cuff 1330 over pneumatic link 1351. Pressure system 1311 and pressure cuff 1330 can be included in sphygmomanometer equipment. Tissue 1340 comprises tissue of a patient under measurement of physiological parameters. Tissue 1340 can comprise an arm, leg, limb, finger, or other tissue element. Measurement system 1310 can include elements described herein for measurement equipment 101 in FIGS. 1-8, although variations are possible.

Each of capacitive sensors 1320-1322 are distributed across pressure cuff 1330 to lie in proximity with tissue 1340 and emit associated electric fields into the surrounding environment of each sensor. When pressure cuff 1330 is placed over tissue 1340 for measurement of blood pressure, sensors 1320-1322 are also placed in proximity to tissue 1340.

Capacitance of each of capacitive sensors 1320-1322 can be employed to detect correct orientation, application, or alignment of pressure cuff 1330 on tissue 1340. For example, pressure cuff 1330 might be applied too loosely, too tightly, be of an incorrect size for the patient, or have poor contact with tissue 1340. As the capacitance measured by each of capacitive sensors 1320-1322 is monitored, these configurations of pressure cuff 1330 can be monitored and alerted. Pressure modulations due to blood pumping in tissue 1340 can induce capacitance modulations in capacitive sensors 1320-1322. These capacitance modulations can be monitored to determine proper magnitudes or amplitudes to establish if correct pressure is being applied by pressure cuff 1330 to tissue 1340.

In other examples, capacitive sensors 1320-1322 can detect where pressure modulations are greatest, and alert an operator of measurement system 1310 to reposition cuff 1330. Greatest modulations are typically preferred in the center of cuff 1330, and capacitive sensors 1320-1322 can be employed by an operator to ensure correct positioning and pressure of cuff 1330 on tissue 1340.

Further examples include measurement system 1310 producing a warning or alarm if an incorrect cuff size or cuff position is used based on cuff pressure measured by capacitive sensors 1320-1322. Measurement system 1310 can illuminate one or more indicator lights, such as LEDs, on cuff 1330 to indicate where the largest pressure modulation or oscillation is presently found, based on pressure measured by capacitive sensors 1320-1322, and an operator can reposition cuff 1330 to align the largest oscillation to the center of cuff 1330 using the indicator lights as a guide. Previous measurements of capacitive sensors 1320-1322 can be stored for later use when re-applying cuff 1330 to help guide cuff inflation or positioning.

Measurement of blood pressure of tissue 1340 can also be enhanced by capacitive sensors 1320-1322. Specifically, a capacitance-based pressure measurement can be determined by each of capacitive sensors 1320-1322. This capacitance-based pressure measurement can be used to adjust pressure of a multi-chamber cuff to adjust pressure of each chamber based on a desired pressure and the capacitance-based measurement of current pressure. Cuff size can be variable based on pressure, and capacitive sensors 1320-1322 can indicate when a desired pressure or size is achieved. Correction of various measurement parameters can also occur based on capacitance-based pressure measurement. For example, regions of cuff 1330 with higher pressure can have a first level of measurement correction included, while regions of cuff 1330 with lower pressure can have a second level of measurement correction included. The correction can include scaling values measured for systolic, diastolic, or mean arterial pressure based on pressure measurements found at each of capacitive sensors 1320-1322. In addition, pressure measurements of cuff 1330 performed by capacitive sensors 1320-1322 can indicate confidence values for the blood pressure measurements, leading to a quality score that scales based on a desired pressure of cuff 1330 and an actual pressure of cuff 1330. Sensors may also aid in smarter cuff inflation and deflation profiles, leading to faster or more accurate measurements with less patient discomfort.

Capacitive sensors 1320-1322 can comprise thin metallic plates, metallic grids, metallic patches, or other capacitor plate materials. Although capacitive sensors 1320-1322 are included in FIG. 13, other sensor types could instead be employed to detect variable pressure of cuff 1330 on tissue 1340, such as impedance sensors, resistance sensors, inductance sensors, or pressure sensors, including combinations thereof.

Figure 14:
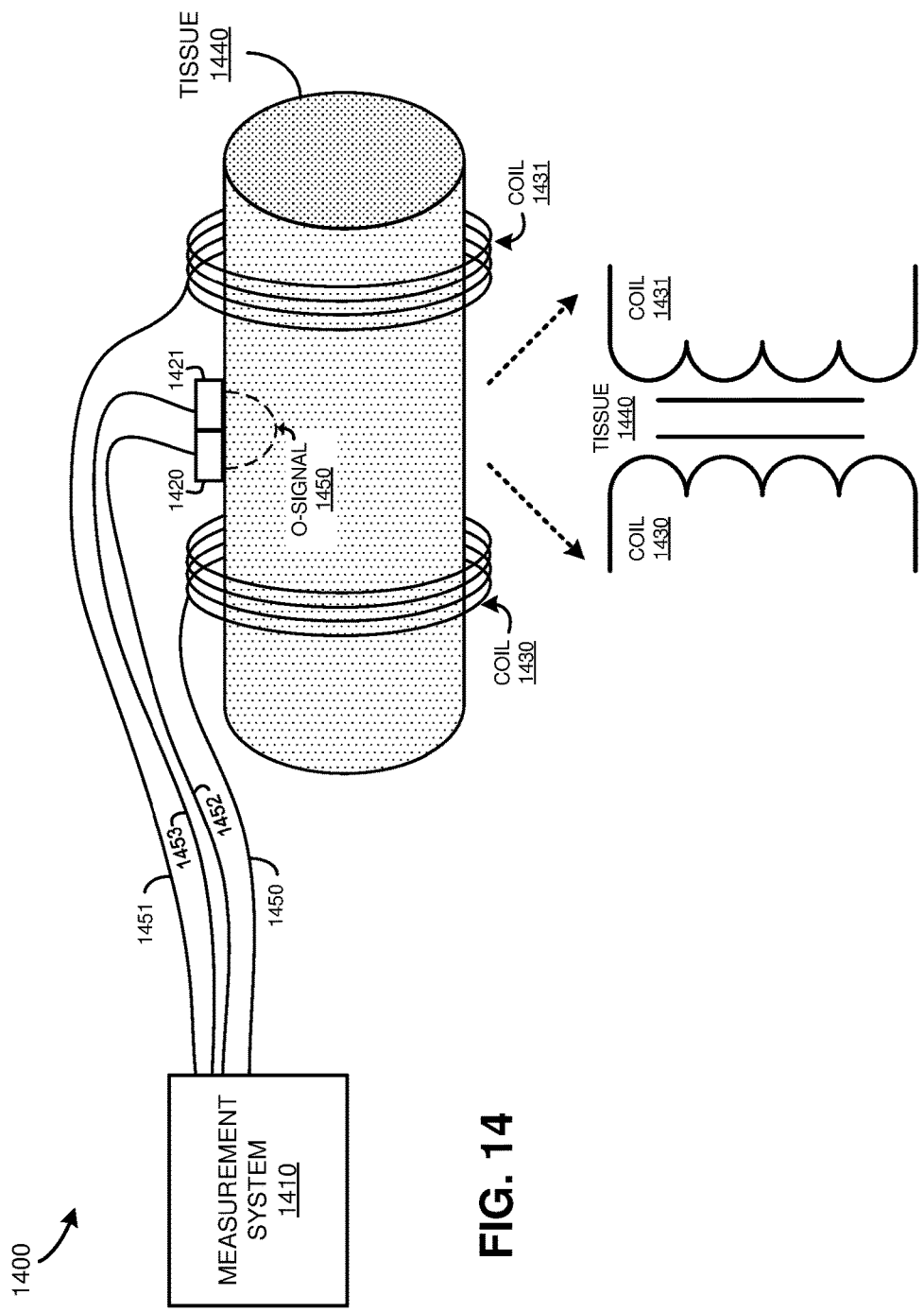
FIG. 14 is a system diagram illustrating a physiological measurement system.

FIG. 14 is a system diagram illustrating physiological measurement system 1400. System 1400 includes measurement system 1410, with optical emitter 1420, optical detector 1421, and inductive coils 1430-1431 applied to tissue 1440. Measurement system 1410 and inductive coil 1430 communicate over link 1450. Measurement system 1410 and inductive coil 1431 communicate over link 1451. Measurement system 1410 and optical emitter 1420 communicate over link 1452. Measurement system 1410 and optical detector communicate over link 1453.

Measurement system 1410 can include elements described for measurement equipment 101 in FIGS. 1-8, although variations are possible. Likewise, optical emitter and optical detector 1420-1421 can include elements described for optical emitter and detector 180-181 in FIG. 1B, although variations are possible. Links 1450-1451 are electric links for carrying a time-based electrical signal to ones of coils 1430-1431. Links 1452-1453 comprise elements described herein for links 160-161, although variations are possible.

An electrical schematic representation of inductive coils 1430-1431 and tissue 1440 is shown at the bottom of FIG. 14. In operation, at least one of coils 1430-1431 are powered by a modulated electrical signal to create a transformer, with tissue 1440 acting as a pseudo-core to the transformer. In one example, coil 1430 acts as a transmitter and coil 1431 acts as a receiver, although the opposite configuration is possible. When operating, magnetic fields will be induced in tissue 1440 by the coils. Tissue 1440 will have a variable magnetic permeability, such as due to changes in blood components, pulsing of arterial or venous blood, among other variations. As the magnetic permeability of tissue 1440 changes with time, parameters such as pulsing of blood, hydration, blood oxygenation, hemoglobin movement, and other physiological measurements can be extracted from the changes in magnetic permeability.

In a first example measurement, variations in magnetic permeability can be detected by measurement system 1410 and these variations can represent a pulsatile waveform. The pulsatile waveform can be indicative of a pulse in tissue 1440. Measurement system 1410 can use this pulsatile waveform to determine physiological parameters, or to supplement and enhance other physiological measurements. For example, optical emitter 1420 emits optical signal 1450 into tissue 1440 and optical detector 1421 detects optical signal 1450 after propagation in tissue 1440. The pulsatile waveform detected using inductive coils 1430-1431 can be used to cross-check a PPG monitored by optical sensors 1420-1421. This cross-check can verify that a PPG signal is valid, or reduce the number of false alarms associated with a PPG monitoring system due to optical sensors improperly applied to tissue 1440 or entirely off of tissue 1440. To verify that a PPG signal is valid, a pulsatile waveform detected using inductive coils 1430-1431 can be correlated or aligned to a PPG measured by optical sensors 1420-1421. If a pulsatile waveform detected using inductive coils 1430-1431 correlates to a PPG measured by optical sensors 1420-1421, then the PPG can be considered valid. However, if the PPG measured by optical sensors 1420-1421 does not correlate or align to that measured using inductive coils 1430-1431, then the PPG can be considered suspect or invalid, and an operator can be notified of a possible discrepancy or error in the measurements.

Figure 15:
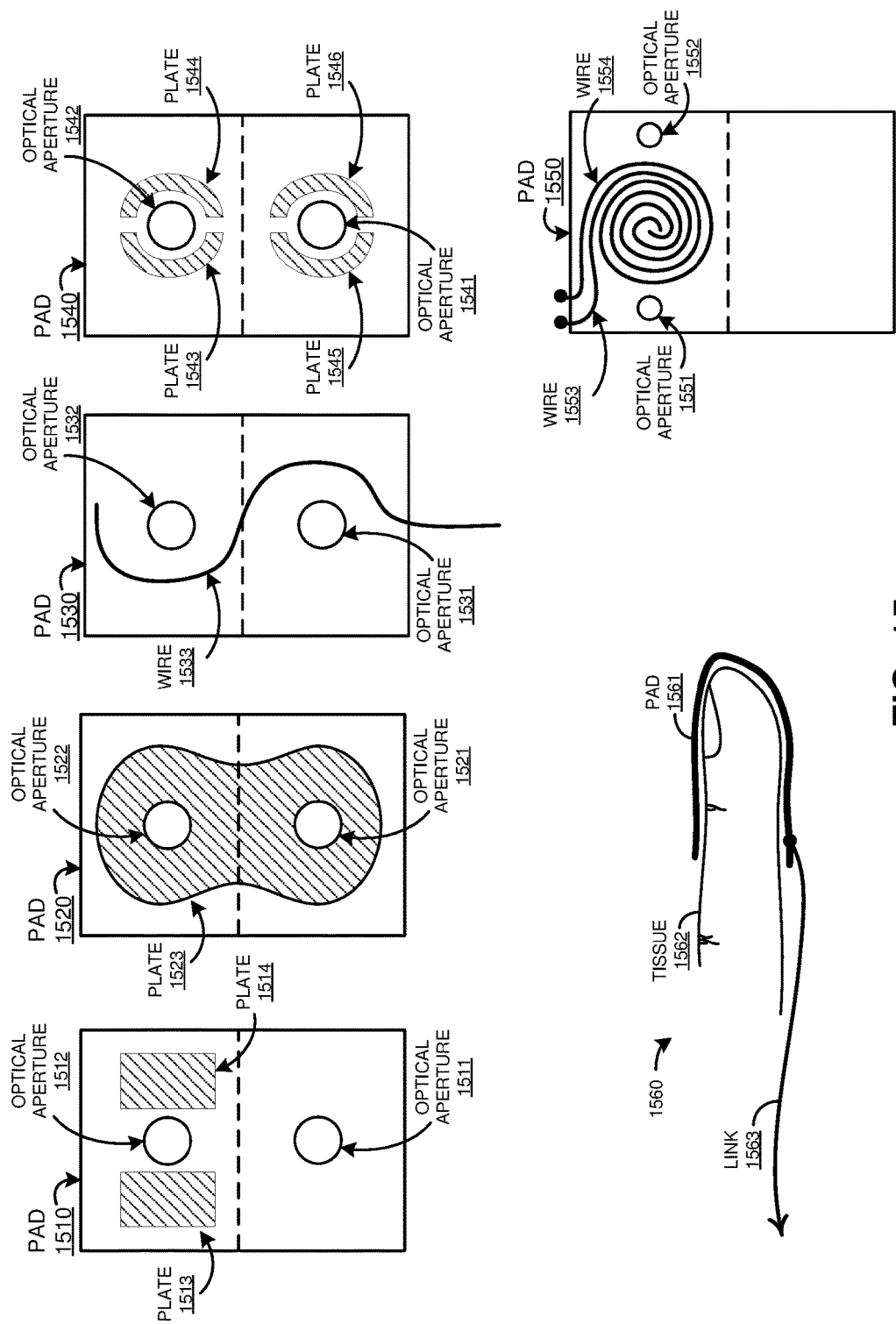
FIG. 15 is a diagram illustrating measurement pads for measurement of physiological parameters.

FIG. 15 is a diagram illustrating measurement pads for measurement of physiological parameters. FIG. 15 includes 5 pad configurations, namely pads 1510, 1520, 1530, 1540, and 1550. Each of pads 1510, 1520, 1530, 1540, and 1550 can comprise any bio compatible material for interfacing with tissue of a patient. Adhesive can be included in any of pads 1510, 1520, 1530, 1540, and 1550 to attach to tissue of a patient, or other mechanical attachment elements can be included, such as clips, springs, bands, and the like. Each of pads 1510, 1520, 1530, 1540, and 1550 can be used for the various capacitive node or optical node sensor elements herein, and other variations are possible. Each measurement pad may be attached to or integrally incorporated into a sensor that is configured to attach to or interface with the tissue to be measured.

As shown in system 1560, an example finger as tissue 1562 has an exemplary pad 1561 applied thereto. Link 1563 supplies any signaling and shielding appropriate for measurement or sensor elements of pad 1561. Pad 1561 can be applied to one side or more than one side of tissue 1562, such as a top and bottom of a finger as shown. Capacitor elements can be included in pad 1561 to lie in proximity to one or both sides of tissue 1562.

Turning now to each of pads 1510, 1520, 1530, 1540, and 1550 each pad is intended to be folded over an extremity, such as a finger or toe, as indicated by the dotted fold line on each pad. Alternatively, each pad can be applied generally flat to tissue such as a forehead, chest, leg, arm, and the like. Although not shown for clarity in FIG. 15, each capacitive element can include an associated electrical link for connection with a measurement system, along with any associated shielding and ground pads. Likewise, optical measurement elements can be included in each pad, with each pad indicating two optical apertures. A first of the optical apertures can be employed for one or more optical emitters, while a second of the optical apertures can be employed for one or more optical detectors. When multiple emitters are included in a pad, more than one optical wavelength can be employed. In some examples, both an optical emitter and detector are employed in each optical aperture, with each optical emitter-detector pair dedicated to a different wavelength of light.

Pad 1510 includes two conductive plates 1513-1514 as capacitor plates. Capacitor plates 1513-1514 are positioned on either side of optical aperture 1512. Capacitor plates 1513-1514 can be flexible and metallic for conforming to tissue once applied with pad 1510. Capacitor plates 1513-1514 can comprise thin metallic sheets, metallic plates, or metallic grids, along with other configurations. Each of capacitor plates 1513-1514 can be employed as a single plate capacitor, or both plates can be combined into a two-plate capacitor. Pad 1510, when wrapped around a finger or toe, or when placed flat onto tissue, can provide two single-plate capacitors on a single side of tissue, or one two-plate capacitor on a single side of tissue.

Pad 1520 includes conductive plate 1523 as a capacitor plate. Capacitor plate 1523 is positioned around both of optical apertures 1521-1522. Capacitor plate 1523 can be flexible and metallic for conforming to tissue once applied with pad 1520. Capacitor plate 1523 can comprise a thin metallic sheet, metallic plate, or metallic grid, along with other configurations. Capacitor plate 1523 can be employed as a single plate capacitor. Pad 1520, when wrapped around a finger or toe, can provide a single-plate capacitor that extends around two sides of tissue. Alternatively, when placed flat onto tissue, pad 1520 can provide a single-plate capacitor that is positioned on one side of tissue.

Pad 1530 includes capacitor plate 1533. Capacitor plate 1533 is positioned around both of optical apertures 1531-1532 in a serpentine fashion. Capacitor plate 1533 can be flexible and metallic for conforming to tissue once applied with pad 1530. Capacitor plate 1533 can comprise a thin metallic wire or narrow flat sheet (such as a circuit trace), along with other configurations. Capacitor plate 1533 can be employed as a single plate capacitor. Pad 1530, when wrapped around a finger or toe, can provide a single-plate capacitor that extends around two sides of tissue. Alternatively, when placed flat onto tissue, pad 1530 can provide a single-plate capacitor that is positioned on one side of tissue.

Pad 1540 includes four conductive plates 1543-1546 as capacitor plates. Capacitor plates 1543-1544 are positioned on either side of optical aperture 1542. Capacitor plates 1545-1546 are positioned on either side of optical aperture 1541. Capacitor plates 1543-1546 can be flexible and metallic for conforming to tissue once applied with pad 1540. Capacitor plates 1543-1546 can comprise thin metallic sheets, metallic plates, or metallic grids, along with other configurations. Each of capacitor plates 1543-1546 can be employed as a single plate capacitor, or in pairs to form two-plate capacitors around each associated optical aperture. Pad 1540, when wrapped around a finger or toe, can provide four single-plate capacitors on two sides of tissue, or two dual-plate capacitors on two sides of tissue. Alternatively, when placed flat onto tissue, pad 1540 can provide various capacitor plate configurations positioned on one side of tissue.

Pad 1550 includes two conductive wires 1553-1554 as capacitor plates. Capacitor plates 1553-1554 are positioned between both of optical apertures 1551-1552 in a spiral fashion. Capacitor plates 1553-1554 can be flexible and metallic for conforming to tissue once applied with pad 1550. Capacitor plates 1553-1554 can comprise thin metallic wires or narrow flat sheets (such as a circuit traces), along with other configurations. Each of capacitor plates 1553-1554 can be employed as a single plate capacitor, or both plates can be combined into a two-plate capacitor. Pad 1550, when wrapped around a finger or toe, can provide a single-plate capacitor that extends around two sides of tissue. Alternatively, when placed flat onto tissue, pad 1550 can provide a single-plate capacitor that is positioned on one side of tissue.

Figure 16:
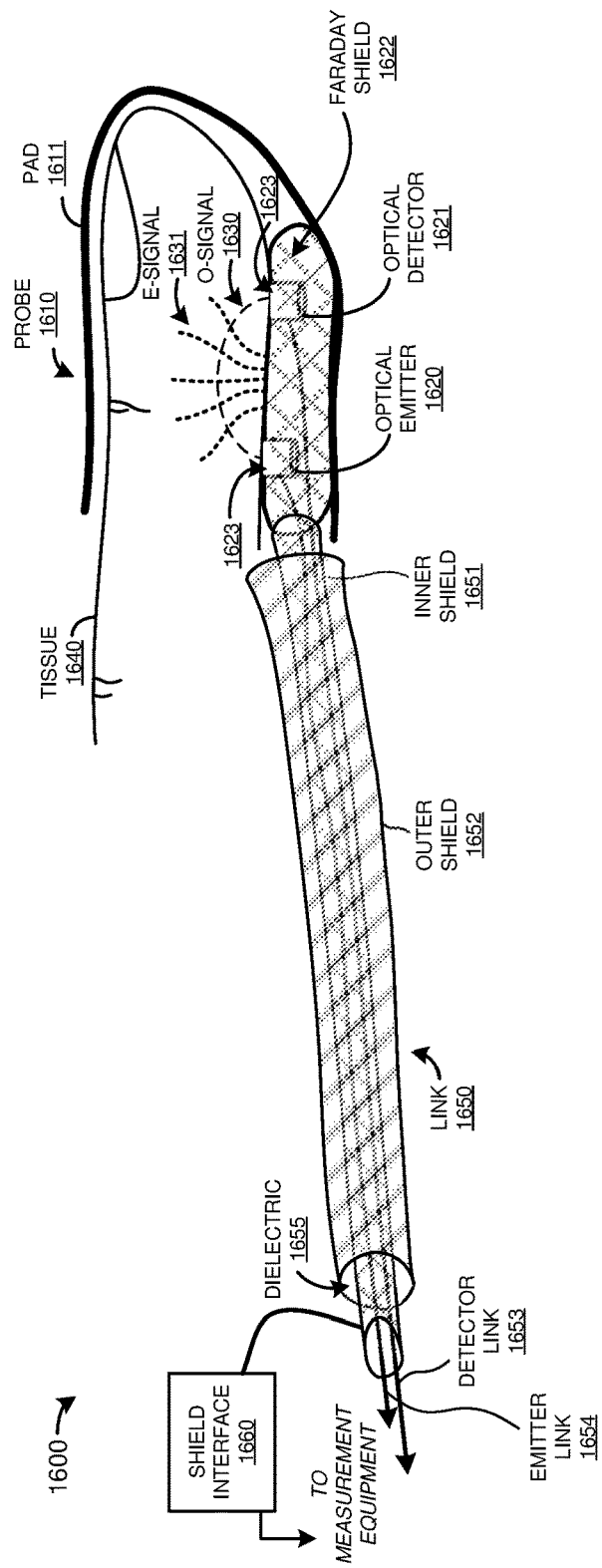
FIG. 16 is a system diagram illustrating a physiological measurement system.

FIG. 16 is a system diagram illustrating physiological measurement system 1600. System 1600 illustrates usage of an electromagnetic shield or faraday shield of a pulse oximetry sensor as a capacitive plate. System 1600 includes pulse oximetry probe 1610, optical emitter 1620, optical detector 1621, faraday shield 1622, measurement link 1650, and shield interface 1660, applied to tissue 1640. Measurement link 1650 is a coaxial link that further includes outer shield 1652, inner shield 1651, detector link 1653, and emitter link 1654. Although one link per emitter/detector is shown in FIG. 16, more the one link can instead be employed. Further measurement equipment, such as processing systems, optical systems, and capacitance systems, are omitted for clarity from FIG. 16.

Pulse oximetry probe 1610 comprises a structural element to position sensing portions of measurement system 1600 onto tissue 1640, such as clips, pads, bands, springs, and the like. In FIG. 16, an example pad 1611 is used as the structural element. Pulse oximetry probe 1610 includes optical emitter 1620 and optical detector 1621 for emitting optical signals 1630 into tissue 1640 for measurement of physiological parameters, such as pulse and $SpO_2$ of blood. In some examples, pulse oximetry probe 1610 comprises a modified MAX-A pulse oximetry probe available from Covidien LP (Boulder, Colo.).

To provide a level of environmental and electromagnetic shielding for at least emitter 1620 and detector 1621, faraday shield 1622 is provided to surround at least emitter 1620 and detector 1621. Faraday shield 1622 comprises a metal or metallic surround or enclosure with associated optical apertures 1623 to allow emission or detection of optical signal 1630. Faraday shield 1622 can comprise a braided shield or wire mesh configuration.

In this example, inner shield 1651 is electrically connected to faraday shield 1622. In some examples, inner shield 1651 is extended to create faraday shield 1622 around at least emitter 1620 and detector 1621. Inner shield 1651 also includes and surrounds emitter link 1654 and detector link 1653. Outer shield 1652 surrounds inner shield 1651, along with any additional wires or links that might be included in link 1650. In this example, outer shield 1652 is not electrically connected to inner shield 1651 and is isolated by dielectric 1655, such as a sheathing or coaxial insulator. Furthermore, outer shield 1652 is not electrically connected to faraday shield 1622 in this example.

In operation, optical signals 1630 are emitted by optical emitter 1620 into tissue 1640 after probe 1610 is applied to tissue 1640. Optical detector 1621 detects optical signal 1630 after propagation through tissue 1640. Optical emitter 1620 and optical detector 1621 communicate with measurement equipment, not shown for clarity, over associated links 1653-1654. Optical emitter 1620 includes LED or laser diode equipment and receives an electrical signal over link 1654. Likewise, optical detector 1621 includes optical detection elements, such as photodiodes, photodetectors, or other optical sensors, and transfers electrical signals representative of the optical signals detected to measurement equipment over link 1653. Inner shield 1651 is provided as an electromagnetic interference (EMI) shield for not only optical emitter 1620 and optical detector 1621, but for also links 1653-1654. In some examples, faraday shield 1622 does not surround optical emitter 1620 and instead surrounds optical detector 1621 and associated links.

Faraday shield 1622 can be employed as a single plate capacitor when placed in proximity to tissue 1640. An ambient electric field can be detected by faraday shield 1622 which can be indicative of proximity to tissue 1640. When an ambient signal is used, then a calibration routine can be performed which establishes measurement thresholds for using faraday shield 1622 as a capacitive plate. These thresholds can indicate when probe 1610 is placed on tissue 1640 or off of tissue 1640. The thresholds can be determined by having an operator take a first measurement when probe 1610 is not on tissue 1640 and a second measurement once probe 1610 is properly placed on tissue 1640. In this manner, measurement equipment can detect when probe 1610 has fallen off or been removed from tissue 1640 and alert monitoring personnel accordingly.

Alternatively, an electrical signal 1631 can be driven onto faraday shield 1622 by inner shield 1651 to emit an electrical signal into tissue 1640 as discussed herein for single plate capacitors. When electrical signals are driven onto faraday shield 1622 by measurement equipment, then processes as discussed herein can be employed to detect when probe 1610 is placed on or is off of tissue 1640. As with the ambient measurement above, appropriate thresholds for probe on/off conditions can be determined. Measurement equipment can then detect when probe 1610 has fallen off or been removed from tissue 1640 and alert monitoring personnel accordingly.

Using faraday shield 1622 as a capacitor plate can introduce noise onto the EMI shielding for at least optical detector 1621. To mitigate this noise, shield interface 1660 can be employed. Shield interface 1660 can include one or more analog switches, digital-to-analog converters, or other high-impedance interface circuitry to isolate inner shield 1651 from measurement equipment attempting to detect sensor on/off conditions. When a measurement for sensor on/off is desired, then measurement equipment can be electrically connected by enabling an analog switch to drive a signal onto inner shield 1651 using a lower impedance connection. Likewise, a normally off high-impedance output of a digital-to-analog converter can be enabled to drive a signal onto inner shield 1651. The measurement signal driven onto inner shield 1651 can be driven by a general purpose 110 pin of a microprocessor as a pulse-width modulated signal, with or without analog filtering.

For example, if an optical measurement using optical emitter 1620 and optical detector 1621 indicates an error condition for the patient undergoing physiological measurement, then before an alert is generated based on the optical measurement, the capacitive measurement using faraday shield 1622 is performed. Shield interface 1660 can drive a measurement signal onto inner shield 1651 which drives electrical field signal 1631 from faraday shield 1622. Based on monitoring this measurement signal a determination can be made whether or not probe 1610 is actually on tissue 1640 or has been removed or fallen off. Alerts for medical personnel or medical logs can be adjusted based on whether probe 1610 is on tissue 1640 or not.

Further methods can be employed to mitigate unwanted interference caused by driving an active signal onto faraday shield 1622 and inner shield 1651. In a first example, inner shield 1651 is driven at more than one modulation frequency at different times, so that resistance and capacitance can be derived from different measurements. In another example, the driven signal is frequency hopped or employs spread spectrum techniques to minimize emitting electromagnetic interference by faraday shield 1622. In yet another example, both inner shield 1651 and outer shield 1652 are driven actively when a capacitance measurement is desired, but each of inner shield 1651 and outer shield 1652 are driven with differential/complementary signals to minimize interference. In further examples, a dummy wire is present in link 1650, or outer shield 1652 is employed as a reference wire, to monitor and cancel environmental interference, such as EMI from lighting, measurement equipment, patients touching conductive objects, ambient EMI, or other sources of EMI. A dummy wire is discussed further in FIG. 17. Regardless of the method, measurement times are typically kept short to minimize interference and to minimize displacement of optical measurements.

Figure 17:
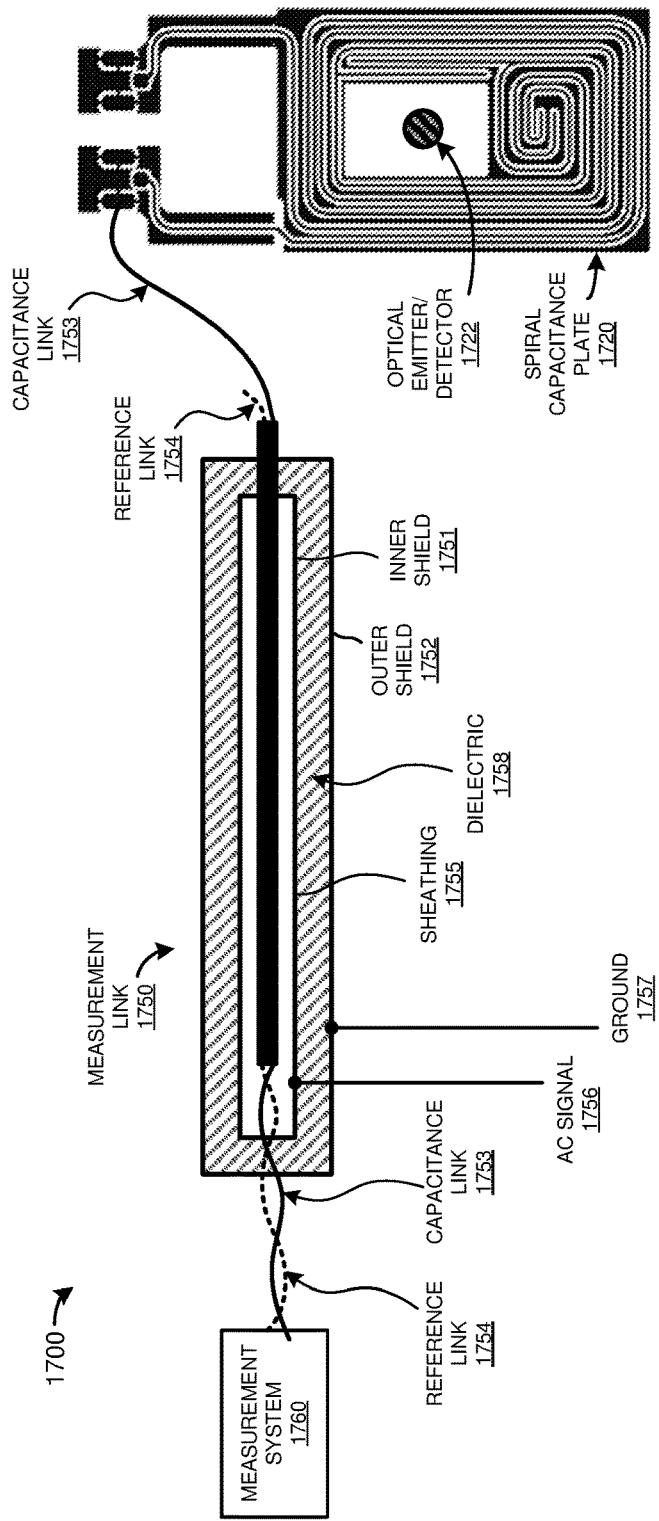
FIG. 17 is a system diagram illustrating a physiological measurement system.

FIG. 17 is a system diagram illustrating physiological measurement system 1700. System 1700 illustrates usage of spiral capacitance plate 1720 along with a differential measurement link arrangement of link 1750. System 1700 includes spiral capacitance plate 1720, optical emitter/detector 1722, measurement link 1750, and measurement system 1760. Spiral capacitance plate 1720 can be applied to tissue, such as a finger or forehead. Measurement link 1750 is a coaxial link with an internal twisted pair of wires. Measurement link 1750 includes outer shield 1752, inner shield 1751, capacitance link 1753, and reference link 1754. Measurement link 1750 can include further capacitance links to interface with plate 1720. Measurement link 1750 can also include optical links or other electrical links used for optical emitter/detector 1722, but these are omitted for clarity in FIG. 17. In some examples, measurement system 1760 comprises a capacitance to digital converter to convert signals detected over link 1753 into a digital format. Further measurement equipment, such as processing systems, optical systems, and capacitance systems, are also omitted for clarity from FIG. 17.

Spiral capacitance plate 1720 comprises structural elements to position sensing portions of measurement system 1700 onto tissue 1740, such as clips, pads, bands, springs, and the like. Spiral capacitance plate 1720 comprises one or more wires, such as circuit traces, that comprise individual capacitor plates. The spiral capacitance wires of plate 1720 allow for larger sensor surface area to sense various physiological parameters in tissue. Plate 1720 can include a single spiral wire or can include multiple, such as two shown in FIG. 17. Plate 1720 includes a central aperture through which optical emitter/detector 1722 can emit/detect optical signals 1730 into tissue for measurement of physiological parameters, such as pulse and $SpO_2$ of blood.

In this example, inner shield 1751 creates a faraday shield around at least links 1753-1754. Inner shield 1751 can be electrically connected to an AC signal source. Outer shield 1752 surrounds inner shield 1751, along with any additional wires or links that might be included in link 1750. Also in this example, outer shield 1752 creates a faraday shield around at least links 1753-1754 and inner shield 1751. Outer shield 1752 is not electrically connected to inner shield 1751 and is isolated by dielectric 1758, which can include sheathing 1755 or coaxial insulator material. Furthermore, outer shield 1752 can be optionally connected to ground or a reference potential.

Measurement link 1750 comprises a two shield system (1751-1752) with a twisted pair wire inside. In the twisted pair, one wire (1753) acts as a conductor for a single plate capacitor 1720 and the second wire (1754) acts as a 'dummy' reference conductor wire. When a person grabs both wires simultaneously, both wires indicate a change in capacitance of a similar magnitude, which can be subtracted out as a common mode signal, leaving behind the desired signal measured using capacitance link 1753. When only capacitance link 1753 or capacitance plate 1720 are contacted or proximate to tissue, then the common mode signal will be smaller and less of a factor in measurement processing. Higher twists per inch in the twisted pair can aid to keep the wires electromagnetically coupled. An electrically driven shield around the twisted pair, such as inner shield 1751, acts as a shield but also can minimize electromagnetic coupling onto the twisted pair, in part because energy will not typically flow between two wires of the same potential. An optional second shield (outer shield 1752) around inner shield 1751 should be grounded to act as a mitigation of radiated emissions from inner shield 1751 when inner shield 1751 is electrically driven, such as by an AC signal. In another example, both inner shield 1751 and outer shield 1752 are driven actively when a capacitance measurement is desired, but each of inner shield 1751 and outer shield 1752 are driven with differential/complementary signals to minimize interference. In further examples, reference link 1754 can be used to monitor and cancel environmental interference, such as EMI from lighting, measurement equipment, patients touching conductive objects, ambient EMI, or other sources of EMI.

In operation, optical signals are emitted by optical emitter/detector 1722 into tissue. Optical emitter/detector 1722 optical signals after propagation through tissue. Optical emitter/detector 1722 communicate with measurement equipment, not shown for clarity, over associated links. Optical emitter/detector 1722 include LED or laser diode equipment and optical detection elements, such as photodiodes, photodetectors, or other optical sensors, and transfers electrical signals representative of the optical signals detected to measurement equipment. Plate 1720 can be employed as a single plate capacitor or two plate capacitor when placed in proximity to tissue. An electrical signal can be driven onto plate 1720 by capacitance link 1753 to emit an electrical signal into tissue as discussed herein for single plate capacitors or two plate capacitors. Measurement system 1760 can monitor changes in an electric field or changes in a capacitance signal associated with the electric field emitted by plate 1720 to determine physiological parameters. Measurement system 1760 can use the capacitance signals to modify or correct measurements performed using the optical elements, among other operations as discussed herein.

Figure 18:
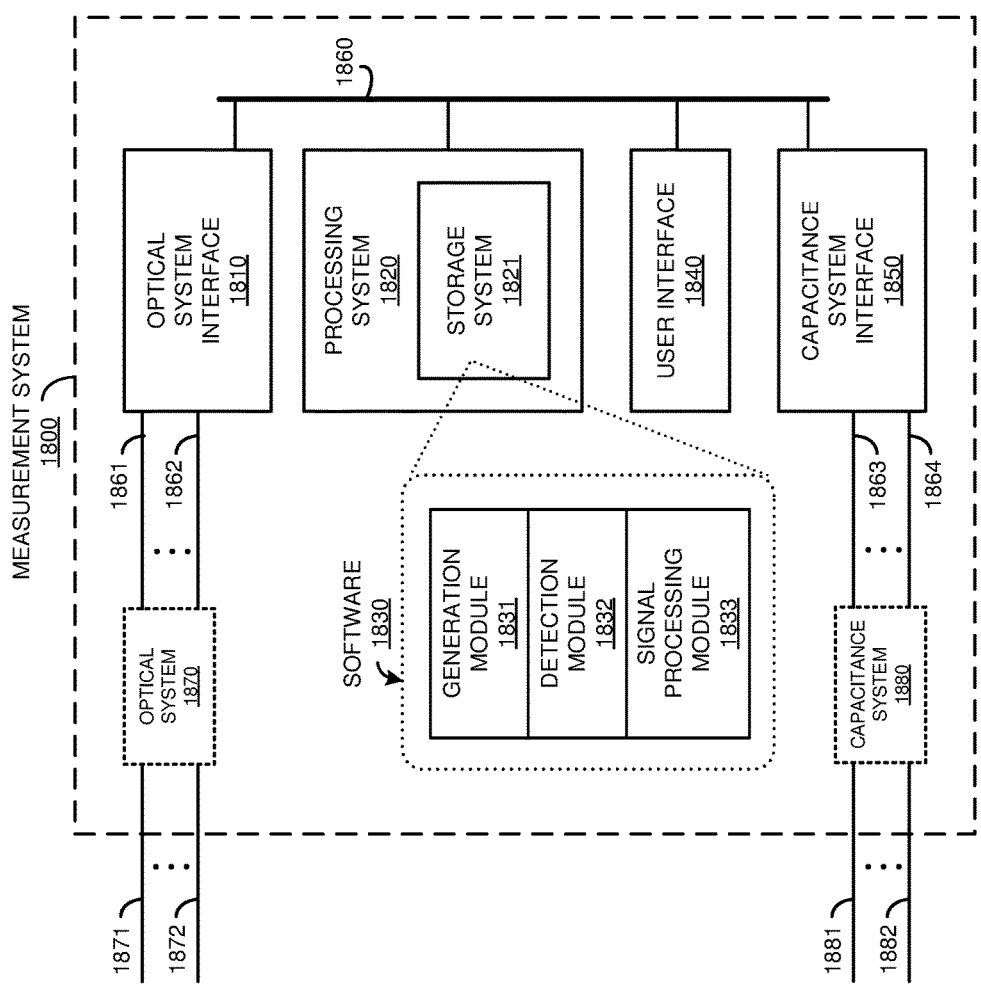
FIG. 18 is a block diagram illustrating a measurement system.

FIG. 18 is a block diagram illustrating measurement system 1800, as an example of elements of measurement equipment 101 in FIGS. 1-8, measurement system 910 in FIG. 9, measurement system 1310 in FIG. 13, or measurement system 1410 in FIG. 14, although these can use other configurations. Measurement system 1800 includes optical system interface 1810, processing system 1820, user interface 1840, capacitance system interface 1850, and optionally optical system 1870 and capacitance system 1880. Optical system interface 1810, processing system 1820, user interface 1840, and capacitance system interface 1850 are shown to communicate over a common bus 1860 for illustrative purposes. It should be understood that discrete links can be employed, such as communication links or other circuitry. Measurement system 1800 may be distributed or consolidated among equipment or circuitry that together forms the elements of measurement system 1800.

Optical system interface 1810 comprises a communication interface for communicating with other circuitry and equipment, such as with optical system 1870. Optical system interface 1810 can include transceiver equipment exchanging communications over one or more of the associated links 1861-1862. It should be understood that optical system interface 1810 can include multiple interfaces, pins, transceivers, or other elements for communicating with multiple external devices. Optical system interface 1810 also receives command and control information and instructions from processing system 1820 or user interface 1840 for controlling the operations of optical system interface 1810. Links 1861-1862 can each use various protocols or communication formats as described herein for links 180-181, including combinations, variations, or improvements thereof.

Processing system 1820 includes storage system 1821. Processing system 1820 retrieves and executes software 1830 from storage system 1821. In some examples, processing system 1820 is located within the same equipment in which optical system interface 1810, user interface 1840, or capacitance system interface 1850 are located. In further examples, processing system 1820 comprises specialized circuitry, and software 1830 or storage system 1821 can be included in the specialized circuitry to operate processing system 1820 as described herein. Storage system 1821 can include a non-transitory computer-readable medium such as a disk, tape, integrated circuit, server, flash memory, or some other memory device, and also may be distributed among multiple memory devices.

Software 1830 may include an operating system, logs, utilities, drivers, networking software, tables, databases, data structures, and other software typically loaded onto a computer system. Software 1830 can contain application programs, server software, firmware, processing algorithms, or some other form of computer-readable processing instructions. When executed by processing system 1820, software 1830 directs processing system 1820 to operate as described herein, such as instruct optical or capacitance systems to generate optical or electrical signals for measurement of physiological parameters of patients, receive signals representative of optical or capacitance measurements of patients, and process at least the received signals to determine physiological parameters of patients, among other operations.

In this example, software 1830 includes generation module 1831, detection module 1832, and signal processing module 1833. It should be understood that a different configuration can be employed, and individual modules of software 1830 can be included in different equipment in measurement system 1800. Generation module 1831 determines parameters for optical or capacitance signals, such as modulation parameters, signal strengths, amplitude parameters, voltage parameters, on/off conditions, or other parameters used in controlling the operation of optical systems and capacitance systems over ones of links 1861-1864. Generation module 1831 directs optical system 1870 and capacitance system 1880 to perform physiological measurements, and can selectively apply or remove power from various detection sensors, emitters, capacitors, and other sensor elements. Detection module 1832 receives characteristics of optical and capacitance signals as detected by external circuitry. Signal processing module 1833 processes the received characteristics of optical and capacitance signals to determine physiological parameters, among other operations.

User interface 1840 includes equipment and circuitry to communicate information to a user of measurement system 1800, such as alerts, measurement results, and measurement status. Examples of the equipment to communicate information to the user can include displays, indicator lights, lamps, light-emitting diodes, haptic feedback devices, audible signal transducers, speakers, buzzers, alarms, vibration devices, or other indicator equipment, including combinations thereof. The information can include blood parameter information, waveforms, summarized blood parameter information, graphs, charts, processing status, or other information. User interface 1840 also includes equipment and circuitry for receiving user input and control, such as for beginning, halting, or changing a measurement process or a calibration process. Examples of the equipment and circuitry for receiving user input and control include push buttons, touch screens, selection knobs, dials, switches, actuators, keys, keyboards, pointer devices, microphones, transducers, potentiometers, non-contact sensing circuitry, or other human-interface equipment.

Capacitance system interface 1850 comprises a communication interface for communicating with other circuitry and equipment, such as with capacitance system 1880. Capacitance system interface 1850 can include transceiver equipment exchanging communications over one or more of the associated links 1863-1864. It should be understood that capacitance system interface 1850 can include multiple interfaces, pins, transceivers, or other elements for communicating with multiple external devices. Capacitance system interface 1850 also receives command and control information and instructions from processing system 1850 or user interface 1840 for controlling the operations of capacitance system interface 1850. Links 1863-1864 can each use various protocols or communication formats as described herein for links 170-171, including combinations, variations, or improvements thereof.

Bus 1860 comprises a physical, logical, or virtual communication link, capable of communicating data, control signals, and communications, along with other information. In some examples, bus 1860 is encapsulated within the elements of measurement system 1800, and may be a software or logical link. In other examples, bus 1860 uses various communication media, such as air, space, metal, optical fiber, or some other signal propagation path, including combinations thereof. Bus 1860 can be a direct link or might include various equipment, intermediate components, systems, and networks.

Optical system 1870 can include electrical to optical conversion circuitry and equipment, optical modulation equipment, and optical waveguide interface equipment. Optical system 1870 can include direct digital synthesis (DDS) components, CD/DVD laser driver components, function generators, oscillators, or other signal generation components, filters, delay elements, signal conditioning components, such as passive signal conditioning devices, attenuators, filters, and directional couplers, active signal conditioning devices, amplifiers, or frequency converters, including combinations thereof. Optical system 1870 can also include switching, multiplexing, or buffering circuitry, such as solid-state switches, RF switches, diodes, or other solid state devices. Optical system 1870 also can include laser elements such as a laser diode, solid-state laser, or other laser device, along with associated driving circuitry. Optical couplers, cabling, or attachments can be included to optically mate to links 1871-1872. Optical system 1870 can also include light detection equipment, optical to electrical conversion circuitry, photon density wave characteristic detection equipment, and analog-to-digital conversion equipment. Optical system 1870 can include one or more photodiodes, phototransistors, avalanche photodiodes (APD), or other optoelectronic sensors, along with associated receiver circuitry such as amplifiers or filters. Optical system 1870 can also include phase and amplitude detection circuitry and processing elements. Links 1871-1872 can each use various signal formats as described herein for links 161-162, including combinations, variations, or improvements thereof.

Capacitance system 1880 comprises one or more electrical interfaces for applying one or more electric field signals to tissue of a patient over electrical links 1881-1882. In some examples, capacitance system 1880 drives one or more capacitor plates that are placed in proximity to tissue of a patient. Capacitance system 1880 can include transceivers, amplifiers, modulators, capacitance monitoring systems and circuitry, impedance matching circuitry, human-interface circuitry, electrostatic discharge circuitry, and electromagnetic shield interface circuitry, including combinations thereof. It should be understood that capacitance system interface 1850 can include multiple interfaces, pins, transceivers, or other elements for communicating with multiple external devices. Capacitance system interface 1880 also can receive command and control information and instructions from capacitance system interface 1850 for controlling the operations of capacitance system 1880. Links 1881-1882 can each use various signal formats as described herein for links 162-168, including combinations, variations, or improvements thereof.

Figure 19:
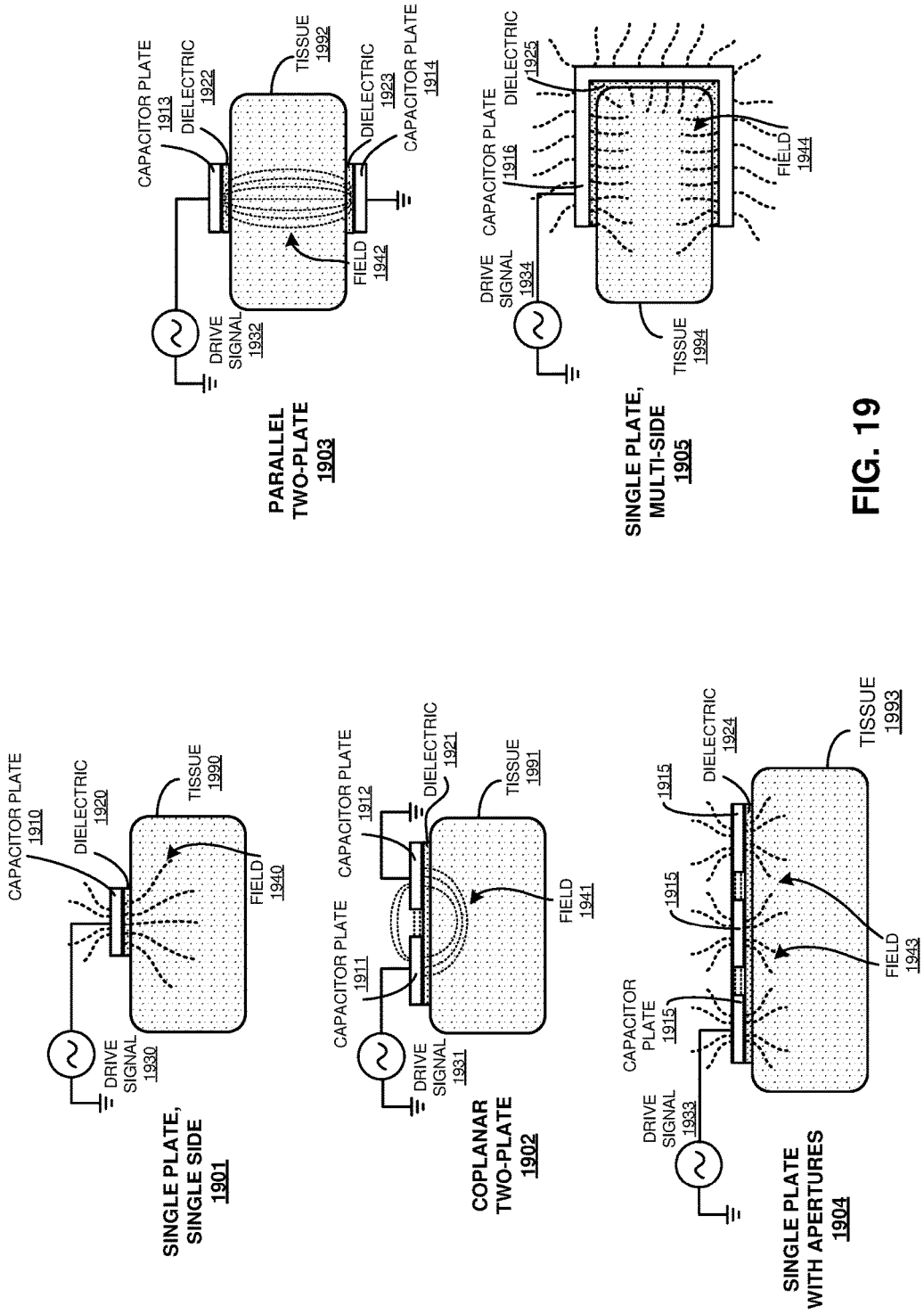
FIG. 19 is a diagram illustrating various capacitance configurations.

FIG. 19 is a diagram illustrating various capacitance configurations. FIG. 19 includes four different capacitance measurement configurations, namely single plate configuration 1901, coplanar two-plate configuration 1902, parallel two-plate configuration 1903, single plate with apertures configuration 1904, and single plate, multi-side configuration 1905. Other capacitor plate configurations are possible, such as discussed herein.

Single plate configuration 1901 includes capacitor plate 1910 which is separated from tissue 1990 by dielectric 1920. In some examples, dielectric 1920 is omitted. Dielectric 1920 can comprise a dielectric material or an air gap, including combinations thereof. Capacitor plate 1910 is driven by drive signal 1930 to produce electric field 1940 in proximity of tissue 1990. In this configuration, field 1940 comprises an electric field which can extend to infinity or can use tissue 1990 as a second capacitive plate. In some examples, tissue 1990 is connected to a ground potential. Configuration 1901 can be an example of capacitance node 182 of FIGS. 1A-1B, capacitance nodes 185-186 in FIG. 5, or capacitance node 187 or 189 in FIG. 7, among others, including variations thereof. In the example shown in FIG. 19, capacitor plate 1910 is positioned on one side of tissue 1990. In further examples, single capacitor plate 1910 can wrap around more than one side of tissue 1990, such as capacitor plate 189 in FIG. 7 or pad 1530 of FIG. 15.

Coplanar two-plate configuration 1902 includes capacitor plates 1911-1912 which are separated from tissue 1991 by dielectric 1921. In some examples, dielectric 1921 is omitted. Dielectric 1921 can comprise a dielectric material or an air gap, including combinations thereof. Capacitor plate 1911 is driven by drive signal 1931 to produce electric field 1941 in proximity of tissue 1991, with capacitor plate 1912 connected to a ground potential. In this configuration, field 1941 comprises an electric field between capacitor plates 1911-1912. The portion of field 1941 that penetrates into tissue 1991 comprises a fringe field of a two-plate capacitor formed by capacitor plates 1911-1912. In some examples, tissue 1991 is connected to a ground potential. Configuration 1902 can be an example of capacitance nodes 183-184 of FIG. 3 or capacitance nodes 187-188 in FIG. 7, among others, including variations thereof. In the example shown in FIG. 19, capacitor plates 1911-1912 are positioned on the same side of tissue 1990.

Parallel two-plate configuration 1903 includes capacitor plates 1913-1914 which are separated from tissue 1992 by associated dielectric 1922-1923. In some examples, dielectric 1922-1923 are omitted. Dielectric 1922-1923 can comprise a dielectric material or an air gap, including combinations thereof. Capacitor plates 1913-1914 are driven by drive signal 1932 to produce electric field 1942 in proximity of tissue 1992, with capacitor plate 1914 connected to a ground potential. In this configuration, field 1942 comprises an electric field between capacitor plates 1913-1914. The portion of field 1942 that penetrates into tissue 1992 comprises a field of a two-plate capacitor formed by capacitor plates 1913-1914. In some examples, tissue 1992 is connected to a ground potential. Configuration 1903 can be an example of pad 1540 of FIG. 15, among others, including variations thereof. In the example shown in FIG. 19, capacitor plates 1913-1914 are positioned on different, opposing, sides of tissue 1990.

Single plate with apertures configuration 1904 includes capacitor plate 1915 which is separated from tissue 1993 by dielectric 1924. In some examples, dielectric 1924 is omitted. Dielectric 1924 can comprise a dielectric material or an air gap, including combinations thereof. Capacitor plate 1915 is driven by drive signal 1933 to produce electric field 1943 in proximity of tissue 1993. In this configuration, field 1943 comprises an electric field which can extend to infinity or can use tissue 1993 as a second capacitive plate. In some examples, tissue 1993 is connected to a ground potential. Configuration 1904 can be an example of pad 1520 of FIG. 15 or pad 17 of FIG. 17. Configuration 1904 can also be an example of capacitance node 182 of FIGS. 1A-1B, capacitance nodes 185-186 in FIG. 5, or capacitance node 187 or 189 in FIG. 7, among others, when one or more apertures are included. In the example shown in FIG. 19, capacitor plate 1915 is positioned on one side of tissue 1993. In further examples, single capacitor plate 1915 can wrap around more than one side of tissue 1993, such as capacitor plate 189 in FIG. 7, pad 1520 of FIG. 15, or configuration 1905 in FIG. 19.

Single plate, multi-side configuration 1905 includes capacitor plate 1916 which is separated from tissue 1994 by dielectric 1925. In some examples, dielectric 1925 is omitted. Dielectric 1925 can comprise a dielectric material or an air gap, including combinations thereof. Capacitor plate 1916 is driven by drive signal 1934 to produce electric field 1944 in proximity of tissue 1994. In this configuration, field 1944 comprises an electric field which can extend to infinity or can use tissue 1994 as a second capacitive plate. In some examples, tissue 1994 is connected to a ground potential. Configuration 1905 can be an example of capacitance node 189 of FIG. 7, or pads 1520 or 1530 of FIG. 15, among others. In the example shown in FIG. 19, capacitor plate 1916 wraps around more than one side of tissue 1994.

The included descriptions and drawings depict specific embodiments to teach those skilled in the art how to make and use the best mode. For the purpose of teaching inventive principles, some conventional aspects have been simplified or omitted. Those skilled in the art will appreciate variations from these embodiments that fall within the scope of the invention. Those skilled in the art will also appreciate that the features described above can be combined in various ways to form multiple embodiments. As a result, the invention is not limited to the specific embodiments described above.

What is claimed is:

1. A physiological measurement system, comprising:
    an optical system configured to emit one or more optical signals into tissue of a patient, and detect the one or more optical signals after propagation through the tissue;
    a capacitance system configured to apply one or more electric field signals to a single side of the tissue to determine a capacitance signal based at least on changes in the one or more electric field signals; and
    a processing system configured to process at least the one or more detected optical signals to determine a first estimate of a physiological parameter of the patient, and process at least the capacitance signal to determine a second estimate of the physiological parameter of the patient.

2. The measurement system of claim 1, comprising:
    the capacitance system configured to apply the one or more electric field signals to the single side of the tissue using one or more capacitor plates that do not contact the tissue.

3. The measurement system of claim 1, comprising:
    the capacitance system configured to apply the one or more electric field signals to the single side of the tissue using a single plate capacitor.

4. The measurement system of claim 1, comprising:
    the capacitance system configured to apply the one or more electric field signals to the single side of the tissue using a two plate capacitor.

5. The measurement system of claim 1, wherein the capacitance system includes at least one capacitor plate, and wherein the processing system is configured to process the capacitance signal to determine a placement of the at least one capacitor plate with respect to the tissue.

6. The measurement system of claim 5, further comprising:
    a user interface configured to generate an alert when the placement comprises the at least one capacitor plate improperly applied to the tissue.

7. A physiological measurement system, comprising:
    an optical system configured to emit one or more optical signals into tissue of a patient, and detect the one or more optical signals after propagation through the tissue;
    a capacitance system configured to apply one or more electric field signals to a single side of the tissue to determine a capacitance signal based at least on changes in the one or more electric field signals, wherein the capacitance system includes at least one capacitor plate; and
    a processing system configured to process at least the one or more detected optical signals and the capacitance signal to determine a physiological parameter of the patient, wherein the processing system is configured to:
    process the capacitance signal to determine a placement of the at least one capacitor plate with respect to the tissue; and
    compare the capacitance signal to a threshold and determine the placement based on the comparison.

8. The measurement system of claim 7, wherein the one or more detected optical signals comprise an optical plethysmograph, and wherein the processing system is configured to adjust the optical plethysmograph based on the capacitance signal.

9. The measurement system of claim 7, wherein the processing system is configured to subtract a scaled version of the capacitance signal from a correlating portion of the one or more detected optical signals.

10. The measurement system of claim 7, wherein the processing system is configured to use the capacitance signal to identify when noise exceeds a threshold in a portion of the one or more detected optical signals, and de-weight the portion of the one or more detected optical signals when determining the physiological parameter.

11. The measurement system of claim 7, wherein the processing system is configured to use the capacitance signal to identify when noise exceeds a threshold in a portion of the one or more detected optical signals, and omit the portion of the one or more detected optical signals when determining the physiological parameter.

12. The measurement system of claim 7, wherein the processing system is configured to use the capacitance signal to identify when noise exceeds a threshold in the one or more detected optical signals and responsively generate an alert.

13. The measurement system of claim 7, wherein the physiological parameter comprises one or more of a respiratory effort, respiratory rate, pulse rate, hemoglobin concentration, oxygen saturation of blood ($SpO_2$), $SpO_2$ variability, apnea condition, arrhythmia, auto regulation, saturation pattern detection, blood pressure, and temporal variability of photoplethysmogram (PPG) parameters.

14. A physiological measurement system, comprising:
an optical system configured to emit one or more optical signals into tissue of a patient, and detect the one or more optical signals after propagation through the tissue; a capacitance system configured to apply one or more electric field signals to a single side of the tissue to determine a capacitance signal based at least on changes in the one or more electric field signals, wherein the capacitance system includes at least one capacitor plate;
a processing system configured to:
identify a body part of the patient to which the one or more electric field signals are applied based at least on the placement;
process the capacitance signal to determine a placement of the at least one capacitor plate with respect to the tissue; and
process at least the one or more detected optical signals and the capacitance signal to determine a physiological parameter of the patient.

15. A physiological measurement system, comprising:
an optical system configured to emit one or more optical signals into tissue of a patient, and detect the one or more optical signals after propagation through the tissue;
a capacitance system configured to apply one or more electric field signals in proximity to the tissue using one or more capacitor plates that do not contact the tissue to determine a capacitance signal; and
a processing system configured to process at least the one or more detected optical signals to determine a first estimate of a physiological parameter of the patient, and process at least the capacitance signal to determine a second estimate of the physiological parameter of the patient.

16. The measurement system of claim 15, comprising:
the capacitance system configured to apply the one or more electric field signals in proximity to a single side of the tissue.

17. The measurement system of claim 16, comprising:
the capacitance system configured to apply the one or more electric field signals in proximity to the single side of the tissue using a single plate capacitor that does not contact the tissue.

18. The measurement system of claim 16, comprising:
the capacitance system configured to apply the one or more electric field signals in proximity to the tissue using a two plate capacitor, wherein each plate of the two plate capacitor does not contact the tissue.

19. The measurement system of claim 15, comprising:
the capacitance system configured to apply the one or more electric field signals in proximity to the tissue using a two plate capacitor, wherein the tissue is positioned between capacitor plates of the two plate capacitor and the capacitor plates do not contact the tissue.

20. The measurement system of claim 15, comprising:
the processing system configured to process the capacitance signal to determine a placement of at least one capacitor plate with respect to the tissue.

21. A physiological measurement system, comprising:
an optical system configured to emit one or more optical signals into tissue of a patient, and detect the one or more optical signals after propagation through the tissue;
a capacitance system configured to apply one or more electric field signals in proximity to the tissue using one or more capacitor plates that do not contact the tissue to determine a capacitance signal; and
a processing system configured to:
process at least the one or more detected optical signals and the capacitance signal to determine a physiological parameter of the patient;
process the capacitance signal to determine a placement of at least one capacitor plate with respect to the tissue; and
compare the capacitance signal to a threshold and determine the placement based on the comparison.

22. A physiological measurement system, comprising:
an optical system configured to emit one or more optical signals into tissue of a patient, and detect the one or more optical signals after propagation through the tissue;
a capacitance system configured to apply one or more electric field signals in proximity to the tissue using one or more capacitor plates that do not contact the tissue to determine a capacitance signal; and
a processing system configured to:
process at least the one or more detected optical signals and the capacitance signal to determine a physiological parameter of the patient; and
process the capacitance signal to determine a placement of at least one capacitor plate with respect to the tissue, wherein the placement comprises a body part of the patient.

23. The measurement system of claim 22, wherein the one or more detected optical signals comprise an optical plethysmograph, and wherein the processing system is configured to adjust the optical plethysmograph with the capacitance signal.

24. The measurement system of claim 22, wherein the processing system is configured to subtract a scaled version of the capacitance signal from a correlating portion of the one or more detected optical signals.

25. The measurement system of claim 22, wherein the processing system is configured to use the capacitance signal to identify when noise exceeds a threshold in a portion of the one or more detected optical signals, and de-weight the portion of the one or more detected optical signals when determining the physiological parameter.

26. The measurement system of claim 22, wherein the processing system is configured to use the capacitance signal to identify when noise exceeds a threshold in a portion of the one or more detected optical signals, and omit the portion of the one or more detected optical signals when determining the physiological parameter.

27. The measurement system of claim 22, wherein the processing system is configured to use the capacitance signal to identify when noise exceeds a threshold in the one or more detected optical signals and responsively generate an alert.

28. The measurement system of claim 22, wherein the physiological parameter comprises one or more of a respiratory effort, respiratory rate, pulse rate, hemoglobin concentration, oxygen saturation of blood ($SpO_2$), $SpO_2$ variability, apnea condition, arrhythmia, auto regulation, saturation pattern detection, blood pressure, and temporal variability of photoplethysmogram (PPG) parameters.

29. A method of operating a physiological measurement system, the method comprising:
emitting one or more optical signals into tissue of a patient, and detecting the one or more optical signals after propagation through the tissue;

applying one or more electric field signals to a single side of the tissue;
determining a capacitance signal based at least on changes in the one or more electric field signals; and
processing at least the one or more detected optical signals to determine a first estimate of a physiological parameter of the patient, and process at least the capacitance signal to determine a second estimate of the physiological parameter of the patient.

30. The method of claim 29, further comprising:
applying the one or more electric field signals to the single side of the tissue using one or more capacitor plates that do not contact the tissue.

* * * * *